US012765756B2

(12) United States Patent
Horiuchi et al.

(10) Patent No.: US 12,765,756 B2
(45) Date of Patent: Oct. 20, 2026

(54) MEDICAL MANIPULATOR SYSTEM AND CONTROL METHOD AND PROCESSOR FOR MEDICAL MANIPULATOR SYSTEM

(71) Applicant: OLYMPUS MEDICAL SYSTEMS CORP., Tokyo (JP)

(72) Inventors: Tatsuya Horiuchi, Yokohama (JP); Kosuke Kishi, Hachioji (JP); Shu Kambe, Hachioji (JP); Noriaki Yamanaka, Hachioji (JP); Ryota Yanagawa, Hachioji (JP); Shota Sawada, Hachioji (JP)

(73) Assignee: OLYMPUS MEDICAL SYSTEMS CORP., Tokyo (JP)

(*) Notice: Subject to any disclaimer, the term of this patent is extended or adjusted under 35 U.S.C. 154(b) by 289 days.

(21) Appl. No.: 18/594,253

(22) Filed: Mar. 4, 2024

(65) Prior Publication Data

US 2024/0298884 A1 Sep. 12, 2024

Related U.S. Application Data

(60) Provisional application No. 63/450,230, filed on Mar. 6, 2023.

(30) Foreign Application Priority Data

Jul. 14, 2023 (JP) ................................ 2023-116167

(51) Int. Cl.
*A61B 1/00* (2006.01)
*A61B 1/005* (2006.01)
*A61B 1/31* (2006.01)

(52) U.S. Cl.
CPC ........ *A61B 1/0052* (2013.01); *A61B 1/00004* (2013.01); *A61B 1/31* (2013.01)

(58) Field of Classification Search
CPC . A61B 1/0051; A61B 1/00006; A61B 1/0052; A61B 1/00004; A61B 1/31; A61B 1/0039; A61B 1/00042; A61B 1/00066; A61B 2034/302; A61B 2034/303;
(Continued)

(56) References Cited

U.S. PATENT DOCUMENTS

2004/0138530 A1* 7/2004 Kawai .................... A61B 1/009
600/152

FOREIGN PATENT DOCUMENTS

JP 2013027466 A 2/2013

* cited by examiner

*Primary Examiner* — Timothy J Neal
(74) *Attorney, Agent, or Firm* — Scully, Scott, Murphy & Presser, P.C.

(57) ABSTRACT

A medical manipulator system includes a medical manipulator comprising a bending portion, an actuator configured to bend the bending portion, a controller comprising an interface configured to which a bending manipulation for bending the bending portion is input, and configured to detect a movement amount of the interface, and a processor configured to control the actuator. The processor calculates displacement of a bending amount of the bending portion for a reference bending amount and causes the actuator to be driven on the basis of a ratio of a second bending amount to the movement amount of the interface calculated so that a difference between a first bending amount calculated on the basis of a driving amount of the actuator and the second bending amount calculated on the basis of the movement amount of the interface is eliminated.

14 Claims, 29 Drawing Sheets

(58) Field of Classification Search
CPC .............. A61B 34/25; A61M 25/0133; A61M 25/0136; A61M 25/0147
See application file for complete search history.

MEDICAL MANIPULATOR SYSTEM AND CONTROL METHOD AND PROCESSOR FOR MEDICAL MANIPULATOR SYSTEM

Priority is claimed on U.S. Provisional Patent Application No. 63/450,230, filed Mar. 6, 2023 and Japanese Patent Application No. 2023-116167, filed Jul. 14, 2023, the content of which is incorporated herein by reference.

TECHNICAL FIELD

The present disclosure relates to a medical manipulator system and a control method and a processor for the medical manipulator system.

BACKGROUND

Conventionally, medical manipulator systems used for observation and treatment in a luminal organ such as a digestive tract are used. In the medical manipulator system, an insertion portion inserted into the luminal organ and the like can be electrically bent and driven. A user can control a bending operation of the insertion portion or the like from a manipulation portion arranged outside of a body.

SUMMARY

For example, Japanese Unexamined Patent Application, First Publication No. 2013-27466 (hereinafter referred to as Patent Document 1) describes an endoscope that controls switching between a free state in which a bending portion passively bends with respect to an external force when an external force is applied to the bending portion driven electrically and a short-circuit state in which a shape of the bending portion is maintained even if the external force is applied.

However, in the case of a medical manipulator system in which a control device controls the bending portion by driving a motor or the like according to a bending manipulation input from a manipulation portion, when an external force is applied to the bending portion and the bending portion is bent, an input element of the manipulation portion does not follow the movement of the bending portion, and a bending amount based on the bending manipulation input to the manipulation portion and an actual bending amount are different, and manipulability is likely to deteriorate.

The present disclosure relates to a medical manipulator system and a control method and a processor for a medical manipulator system with improved manipulability.

In an example, a medical manipulator system including: a medical manipulator comprising a bending portion capable of being bent; an actuator configured to bend the bending portion; a controller comprising an interface to which a bending manipulation for bending the bending portion is input, and configured to detect a movement amount from an origin of the interface, the interface being capable of moving at least in a first direction away from the origin and a second direction returning to the origin; and a processor communicatively connected to the controller and configured to control the actuator on the basis of the bending manipulation, wherein the processor calculates displacement of a bending amount of the bending portion for a reference bending amount to be taken by the bending portion when the interface is located at the origin and compares a first bending amount that is displacement of the bending amount calculated on the basis of a driving amount of the actuator with a second bending amount that is displacement of the bending amount calculated on the basis of the movement amount of the interface, calculates a ratio of the second bending amount to the movement amount of the interface so that a difference between the first bending amount and the second bending amount is eliminated, and causes the actuator to be driven on the basis of the ratio.

DETAILED DESCRIPTION

First Embodiment

Figure 1:
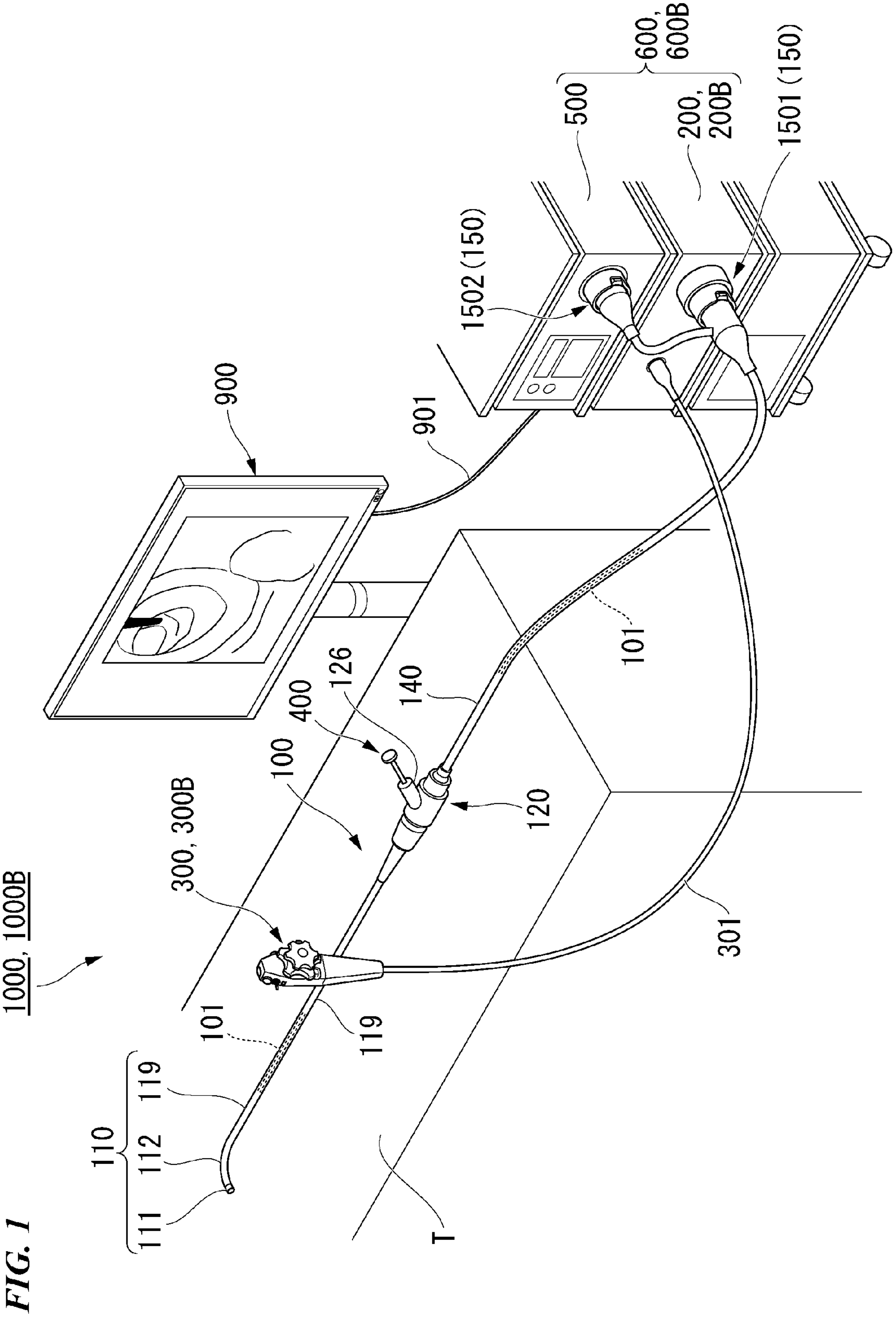
FIG. 1 is an overall view of a medical manipulator system according to a first embodiment.

A motorized endoscope system 1000 according to the first embodiment of the present invention will be described with reference to FIGS. 1 to 19. FIG. 1 is an overall view of the motorized endoscope system 1000 according to the present embodiment. The motorized endoscope system 1000 is an example of a medical manipulator system. Medical manipulators include electrically driven endoscopes, catheters, treatment tools, endoluminal devices, and the like that are inserted into the body.

[Motorized Endoscope System 1000]

The motorized endoscope system 1000 is a medical system that observes and treats the inside of a body of a patient P lying on an operating table T. The motorized endoscope system 1000 includes an endoscope 100, a drive device 200, a controller 300, a treatment tool 400, a video control device 500, and a display device 900.

The endoscope 100 is a device that is inserted into the lumen of the patient P to observe and treat an affected area, and is an example of a medical manipulator. The endoscope 100 is removably attached to the drive device 200. An internal path 101 is formed inside of the endoscope 100. In the following description, in the endoscope 100, the side inserted into the lumen of the patient P is referred to as a "distal end side (distal side) A1" and the side attached to the drive device 200 is referred to as a "proximal end side (proximal side) A2."

The drive device 200 is removably connected to the endoscope 100 and the controller 300. The drive device 200 drives a built-in motor to electrically drive the endoscope 100 on the basis of a manipulation input to the controller 300. Also, the drive device 200 drives a built-in pump or the like to cause the endoscope 100 to perform air supply/suction on the basis of the manipulation input to the controller 300.

The controller 300 is removably connected to the drive device 200 via a manipulation cable 301. The controller 300 may be able to communicate with the drive device 200 through wireless communication instead of wired communication. The physician S can electrically drive the endoscope 100 by manipulating the controller 300.

The treatment tool 400 is a device that passes through the internal path 101 of the endoscope 100 and is inserted into the lumen of the patient P to treat an affected area. In FIG. 1, the treatment tool 400 is inserted from a forceps port 126 into the internal path 101 of the endoscope 100.

The video control device 500 is removably connected to the endoscope 100 and acquires an image captured from the endoscope 100. The video control device 500 causes the display device 900 to display the captured image acquired from the endoscope 100 or a GUI image or a CG image for the purpose of providing information to a manipulator.

The drive device 200 and the video control device 500 constitute a control device 600 that controls the motorized endoscope system 1000. The control device 600 may further include a peripheral device such as a video printer. The drive device 200 and the video control device 500 may be an integrated device.

The display device 900 is a device capable of displaying an image such as an LCD. The display device 900 is connected to the video control device 500 via the display cable 901.

Figure 2:
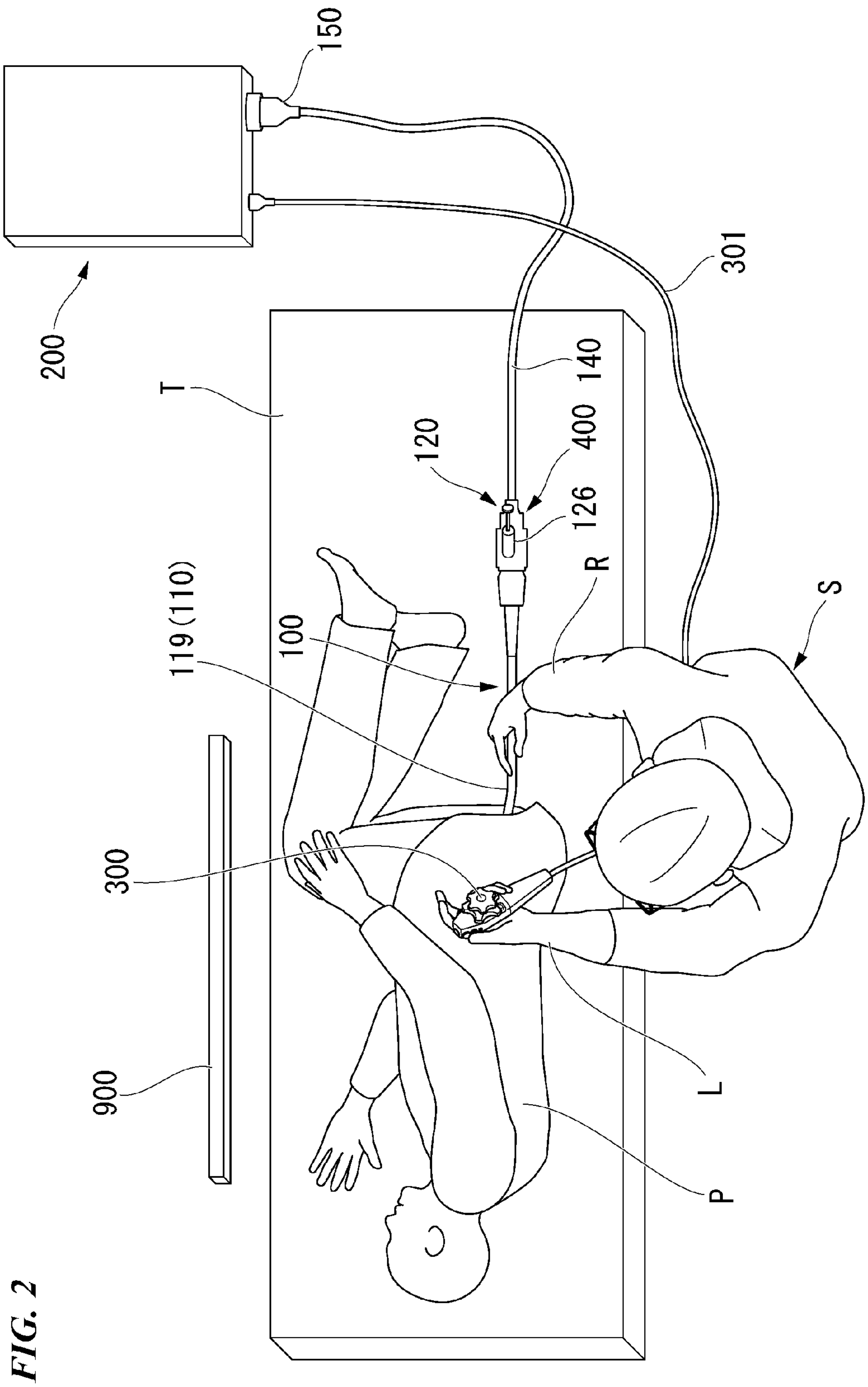
FIG. 2 is a diagram showing an endoscope and a controller of the medical manipulator system used by a physician.

FIG. 2 is a diagram showing the endoscope 100 and the controller 300 used by the physician S.

For example, while observing the imaging image displayed on the display device 900, the physician S manipulates the endoscope 100 inserted into the lumen from the anus of the patient P with his or her right hand R and manipulates the controller 300 with his or her left hand L. Because the endoscope 100 and the controller 300 are separated, the physician S can independently manipulate the endoscope 100 and the controller 300 without either affecting the other.

[Endoscope 100]

Figure 6:
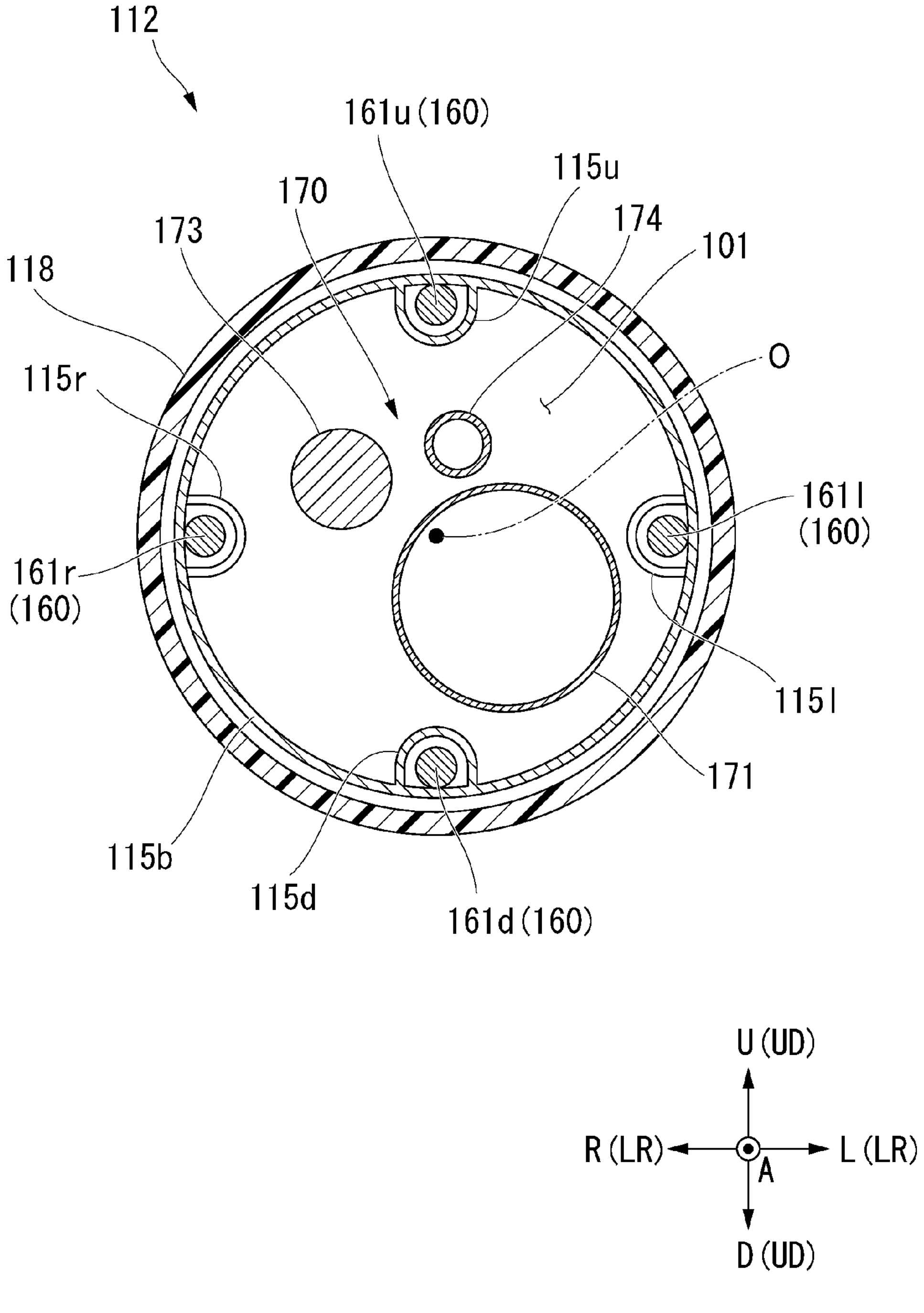
FIG. 6 is a cross-sectional view of the bending portion along line C1-C1 of FIGS. 4 and 5.

As shown in FIG. 1, the endoscope 100 includes an insertion portion 110, a connection portion 120, an extracorporeal soft portion 140, an attachment/detachment portion 150, a bending wire 160 (see FIG. 6), and a built-in object 170 (see FIG. 6). The insertion portion 110, the connection portion 120, the extracorporeal soft portion 140, and the attachment/detachment portion 150 are connected in order from the distal end side A1.

Figure 3:
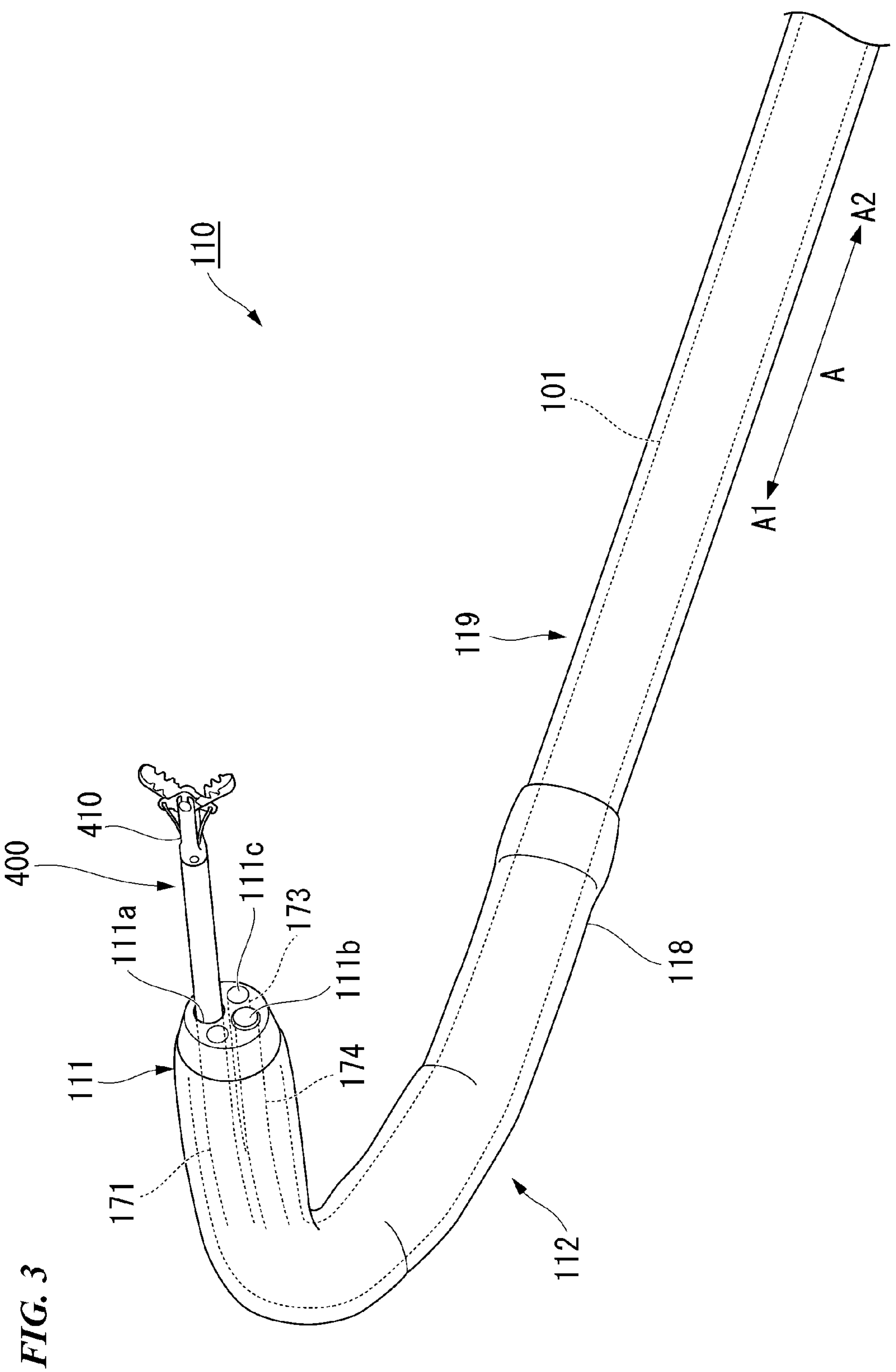
FIG. 3 is a diagram showing an insertion portion of the endoscope.

FIG. 3 is a diagram showing the insertion portion 110 of the endoscope 100.

Inside the endoscope 100, the internal path 101 extending in a longitudinal direction A of the endoscope 100 from the distal end of the insertion portion 110 to the proximal end of the attachment/detachment portion 150 is formed. The bending wire 160 and the built-in object 170 are inserted into the internal path 101.

The built-in object 170 includes a channel tube 171, an air supply/suction tube 172 (see FIG. 10), an imaging cable 173, and a light guide 174.

[Insertion Portion 110]

The insertion portion 110 is an elongated long member that can be inserted into the lumen. The insertion portion 110 includes a distal end portion 111, a bending portion 112, and an intracorporeal soft portion 119. The distal end portion 111, the bending portion 112, and the intracorporeal soft portion 119 are connected in order from the distal end side A1.

As shown in FIG. 3, the distal end portion 111 includes an opening 111*a*, an illumination portion 111*b*, and an imaging portion 111*c*. The opening 111*a* is an opening that communicates with the channel tube 171. As shown in FIG. 3, a treatment portion 410 such as a gripping forceps provided at the distal end of the treatment tool 400 passing through the channel tube 171 protrudes from the opening 111*a*.

The illumination portion 111*b* is connected to the light guide 174 that guides illumination light and emits illumination light for illuminating an imaging target. The imaging portion 111*c* includes an imaging element such as a CMOS and is an imaging device that captures an image of the imaging target. An imaging signal is sent to the video control device 500 via the imaging cable 173.

Figure 4:
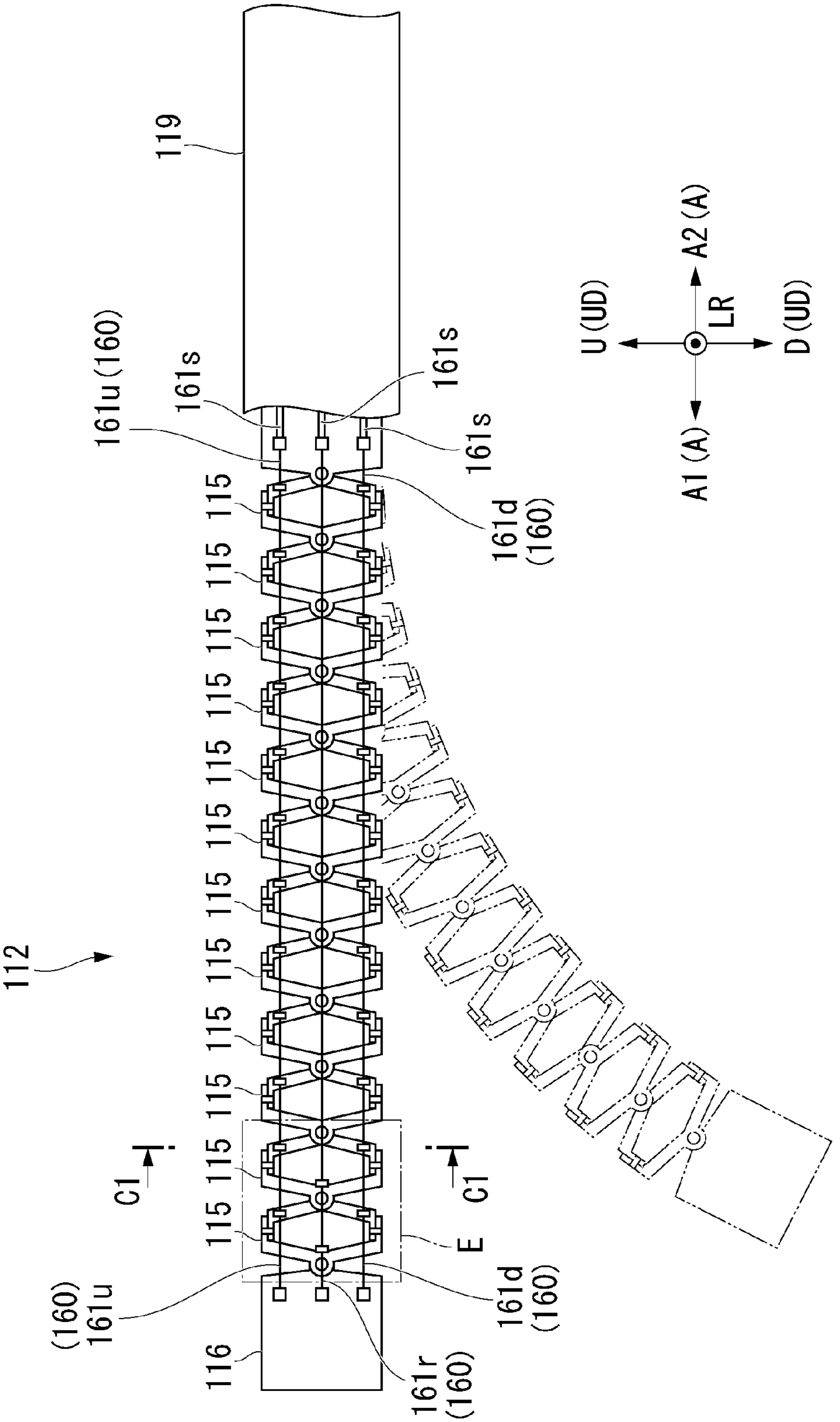
FIG. 4 is a diagram showing a part of a bending portion of the insertion portion in a cross-sectional view.

FIG. 4 is a diagram showing a part of the bending portion 112 in a cross-sectional view.

The bending portion 112 includes a plurality of joint rings (also referred to as bending pieces) 115, a distal end portion 116 connected to the distal ends of the plurality of joint rings 115, and an outer sheath 118 (see FIG. 3). The plurality of joint rings 115 and the distal end portion 116 are connected in the longitudinal direction A inside the outer sheath 118. Also, the shape and number of the joint rings 115 provided in the bending portion 112 are not limited to the shape and number of the joint rings 115 shown in FIG. 4.

Figure 5:
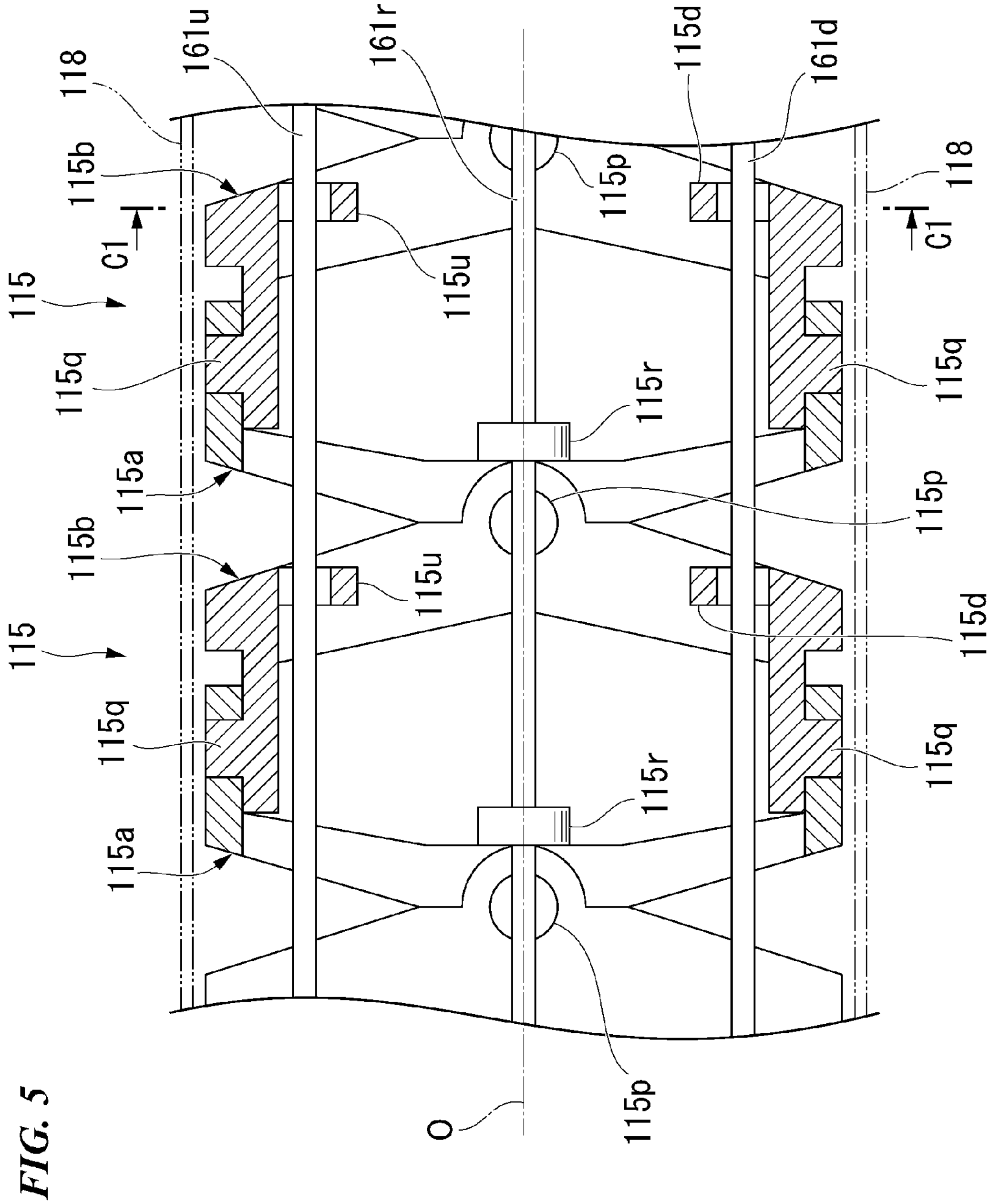
FIG. 5 is an enlarged view of joint rings of the bending portion in an area E shown in FIG. 4.

FIG. 5 is an enlarged view of joint rings 115 in an area E shown in FIG. 4.

The joint ring 115 is a short tubular member formed of metal. The plurality of joint rings 115 are connected to have a space where internal spaces of the adjacent joint rings 115 are continuous.

The joint ring 115 includes a first joint ring 115*a* on the distal end side A1 and a second joint ring 115*b* on the proximal end side A2. The first joint ring 115*a* and the second joint ring 115*b* are rotatably connected by a first rotation pin 115*p* in an upward/downward direction (also referred to as a "UD direction") perpendicular to a longitudinal direction A.

Also, the first joint ring 115*a* and the second joint ring 115*b* are rotatably connected by a second rotation pin 115*q* in a left/right direction (also referred to as an "LR direction") perpendicular to the longitudinal direction A and the UD direction.

The first joint ring 115*a* and the second joint ring 115*b* are alternately connected by the first rotation pin 115*p* and the second rotation pin 115*q* and the bending portion 112 is bendable in a desired direction.

FIG. 6 is a cross-sectional view of the bending portion 112 along line C1-C1 of FIGS. 4 and 5.

On an inner circumferential surface of the second joint ring 115*b*, an upper wire guide 115*u* and a lower wire guide 115*d* are formed. The upper wire guide 115*u* and the lower wire guide 115*d* are arranged on both sides in the UD direction across a central axis O in the longitudinal direction A. On an inner circumferential surface of the first joint ring 115*a*, a left wire guide 1151 and a right wire guide 115*r* are formed. The left wire guide 1151 and the right wire guide 115*r* are arranged on both sides in the LR direction across the central axis O in the longitudinal direction A.

The upper wire guide 115*u*, the lower wire guide 115*d*, the left wire guide 1151, and the right wire guide 115*r* have through-holes into which the bending wire 160 is inserted in the longitudinal direction A.

The bending wire 160 is a wire that bends the bending portion 112. The bending wire 160 extends to the attachment/detachment portion 150 through the internal path 101. As shown in FIGS. 4 and 6, the bending wire 160 has an upper bending wire 161*u*, a lower bending wire 161*d*, a left bending wire 161*l*, a right bending wire 161*r*, and four wire sheaths 161*s*.

As shown in FIG. 4, the upper bending wire 161*u*, the lower bending wire 161*d*, the left bending wire 161*l*, and the right bending wire 161*r* each pass through wire sheaths 161*s*. The distal end of the wire sheath 161*s* is attached to the joint ring 115 at the proximal end of the bending portion 112. The wire sheath 161*s* extends to the attachment/detachment portion 150.

The upper bending wire 161*u* and the lower bending wire 161*d* are wires that bend the bending portion 112 in the UD direction. The upper bending wire 161*u* passes through the upper wire guide 115*u*. The lower bending wire 161*d* passes through the lower wire guide 115*d*.

The distal ends of the upper bending wire 161*u* and the lower bending wire 161*d* are fixed to the distal end portion 116 of the distal end of the bending portion 112, as shown in FIG. 4. The distal ends of the upper bending wire 161*u* and the lower bending wire 161*d* fixed to the distal end portion 116 are arranged on both sides in the UD direction across the central axis O in the longitudinal direction A.

The left bending wire 161*l* and the right bending wire 161*r* are wires that bend the bending portion 112 in the LR direction. The left bending wire 161*l* passes through the left wire guide 1151. The right bending wire 161*r* passes through the right wire guide 115*r*.

The distal ends of the left bending wire 161*l* and the right bending wire 161*r* are fixed to the distal end portion 116 of the bending portion 112 as shown in FIG. 4. The distal ends of the left bending wire 161*l* and the right bending wire 161*r* fixed to the distal end portion 116 are arranged on both sides in the LR direction across the central axis O in the longitudinal direction A.

The bending portion 112 can be bent in the desired direction by pulling or relaxing the bending wires 160 (the upper bending wire 161*u*, the lower bending wire 161*d*, the left bending wire 161*l*, and the right bending wire 161*r*).

As shown in FIG. 6, a bending wire 160, a channel tube 171, an imaging cable 173, and a light guide 174 are inserted into the internal path 101 formed inside of the bending portion 112.

The intracorporeal soft portion 119 is a long and flexible tubular member. The bending wire 160, the channel tube 171, the imaging cable 173, and the light guide 174 are inserted into the internal path 101 formed in the intracorporeal soft portion 119.

[Connection Portion 120]

As shown in FIG. 1, the connection portion 120 is a member that connects the intracorporeal soft portion 119 of the insertion portion 110 and the extracorporeal soft portion 140. The connection portion 120 includes the forceps port 126 that is an insertion port for inserting the treatment tool 400.

[Extracorporeal Soft Portion 140]

The extracorporeal soft portion 140 is a long tubular member. The bending wire 160, the imaging cable 173, the light guide 174, and the air supply/suction tube 172 (see FIG. 10) are inserted into the internal path 101 formed inside of the extracorporeal soft portion 140.

[Attachment/Detachment Portion 150]

As shown in FIG. 1, the attachment/detachment portion 150 includes a first attachment/detachment portion 1501 attached to the drive device 200 and a second attachment/detachment portion 1502 attached to the video control device 500. Also, the first attachment/detachment portion 1501 and the second attachment/detachment portion 1502 may be an integrated attachment/detachment portion.

The internal path 101 formed inside of the extracorporeal soft portion 140 branches into the first attachment/detachment portion 1501 and the second attachment/detachment portion 1502. The bending wire 160 and the air supply/suction tube 172 pass through the first attachment/detachment portion 1501. The imaging cable 173 and the light guide 174 pass through the second attachment/detachment portion 1502.

Figure 7:
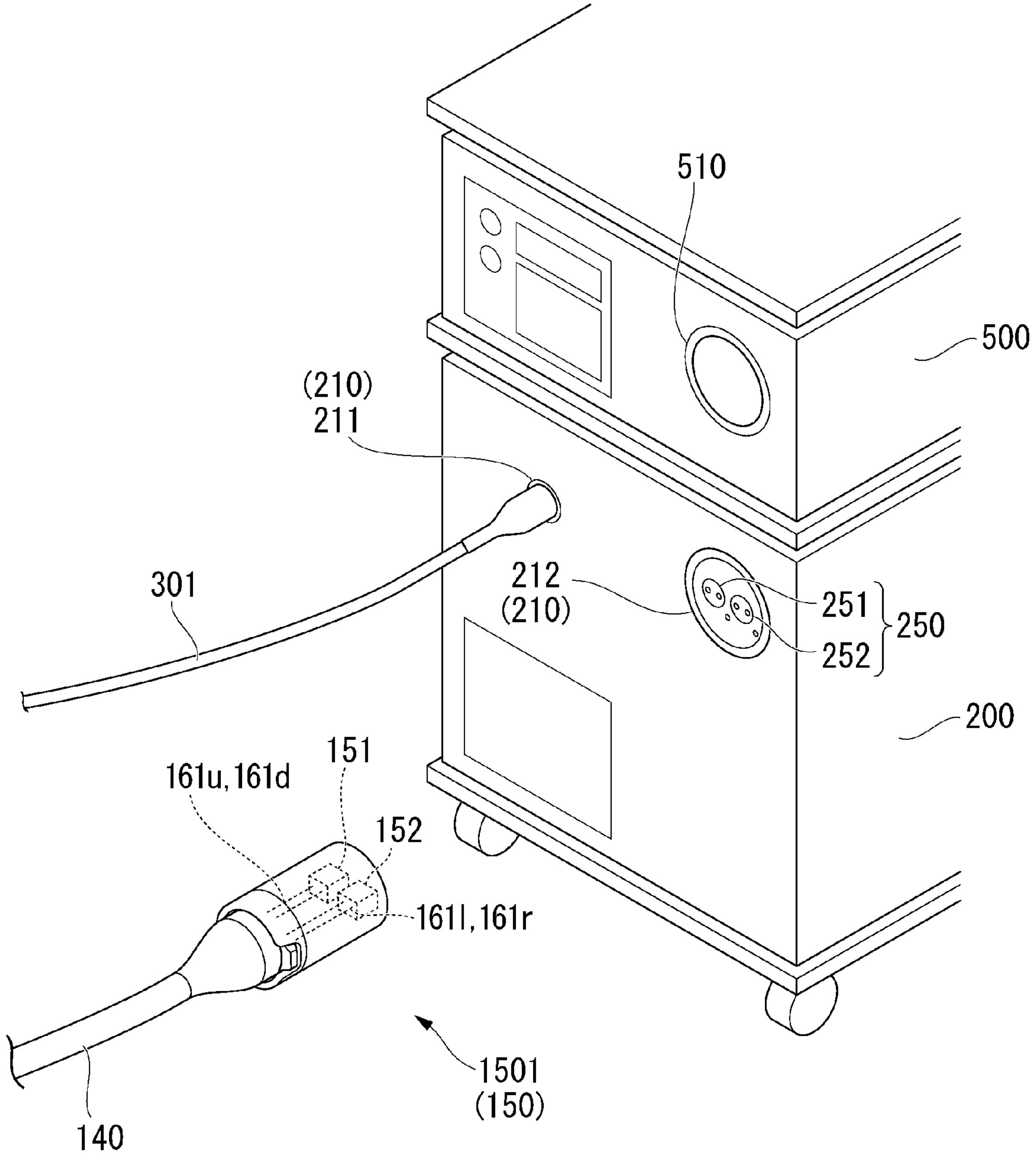
FIG. 7 is a diagram showing a first attachment/detachment portion before attachment to the drive device of the medical manipulator system.

FIG. 7 is a diagram showing the first attachment/detachment portion 1501 before attachment to the drive device 200.

The first attachment/detachment portion 1501 includes an upper/lower bending wire attachment/detachment portion 151 and a left/right bending wire attachment/detachment portion 152.

The upper/lower bending wire attachment/detachment portion 151 is a mechanism that removably connects wires (the upper bending wire 161*u* and the lower bending wire 161*d*), which bend the bending portion 112 in the UD direction, to the drive device 200.

The left/right bending wire attachment/detachment portion 152 is a mechanism that removably connects wires (the left bending wire 161*l* and the right bending wire 161*r*), which bend the bending portion 112 in the LR direction, to the drive device 200.

Because the left/right bending wire attachment/detachment portion 152 has a structure similar to that of the upper/lower bending wire attachment/detachment portion 151, illustration and description thereof are omitted.

Figure 8:
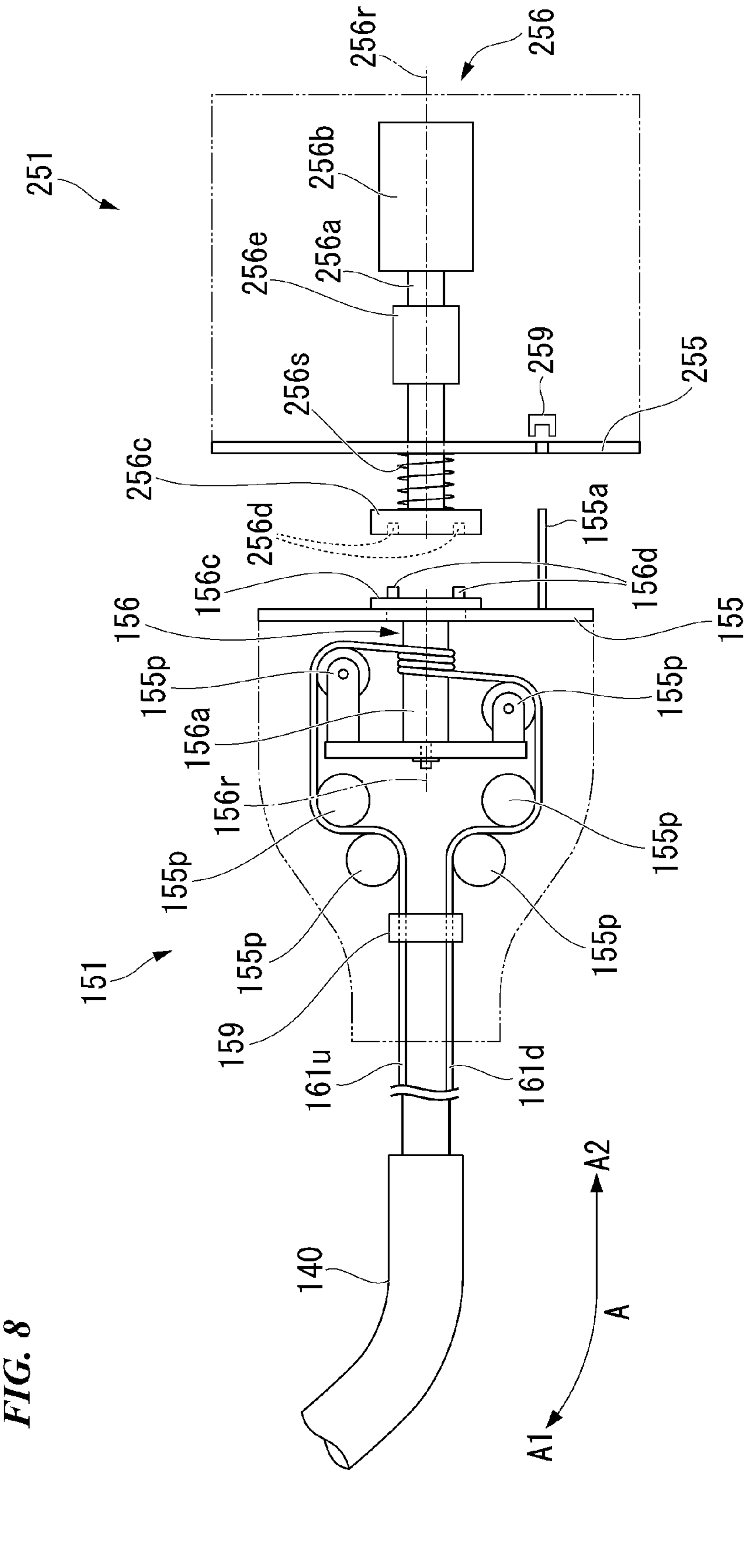
FIG. 8 is a diagram showing an upper/lower bending wire attachment/detachment portion before attachment to the drive device.
Figure 9:
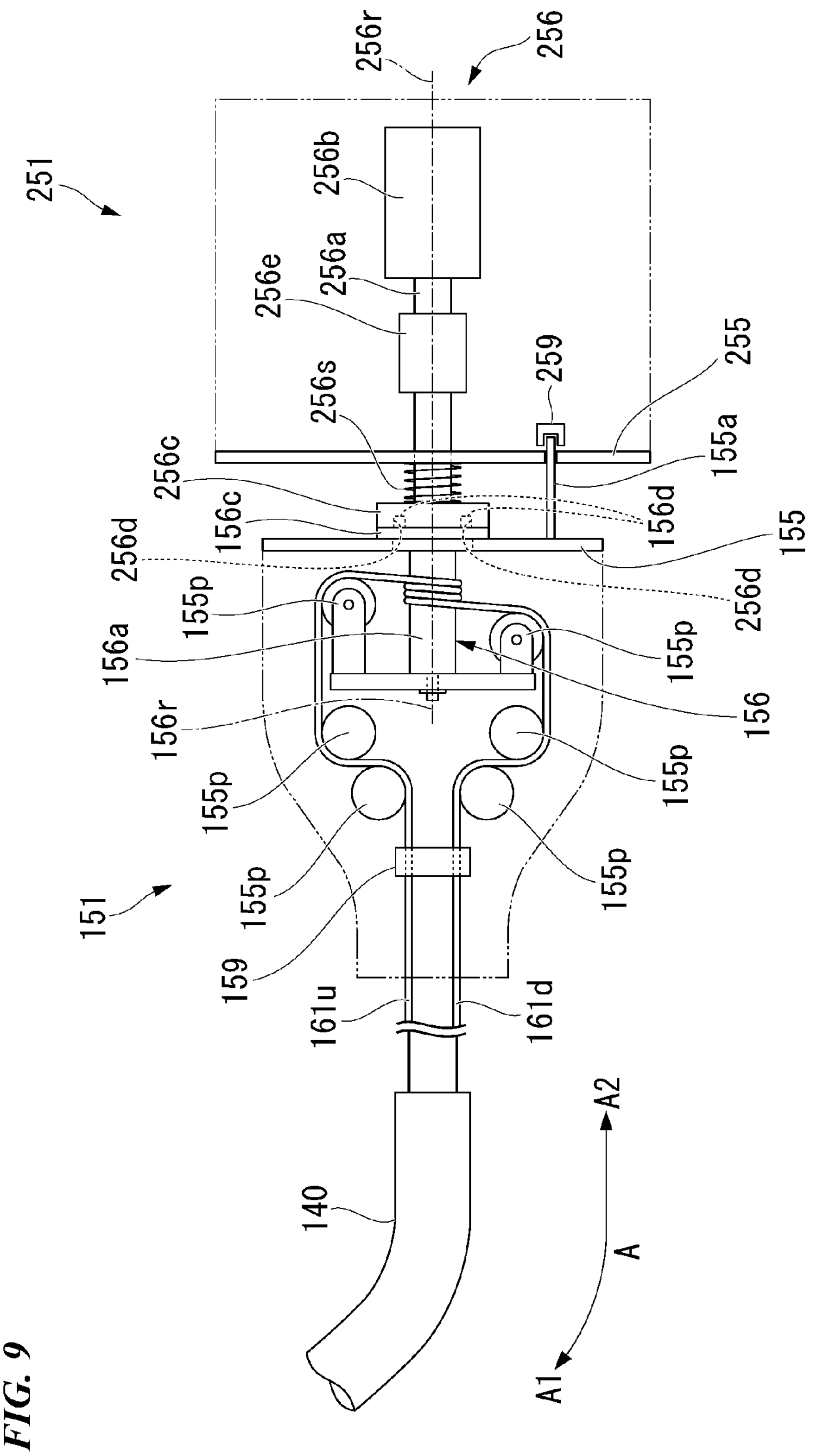
FIG. 9 is a diagram showing the upper/lower bending wire attachment/detachment portion attached to the drive device.

FIG. 8 is a diagram showing the upper/lower bending wire attachment/detachment portion 151 before attachment to the drive device 200. FIG. 9 is a diagram showing the upper/lower bending wire attachment/detachment portion 151 attached to the drive device 200. The upper/lower bending wire attachment/detachment portion 151 includes a support member 155, a rotation drum 156, and a tension sensor 159.

The support member 155 supports the rotation drum 156. The support member 155 includes an attachment/detachment detection dog 155*a*, which is exposed on the proximal end side of the upper/lower bending wire attachment/detachment portion 151, and a plurality of bend pulleys 155*p*.

The bend pulley 155*p* changes a transport direction of the upper bending wire 161*u* passing through the extracorporeal soft portion 140 and guides the upper bending wire 161*u* to the rotation drum 156. Also, the bend pulley 155*p* changes a transport direction of the lower bending wire 161*d* passing through the extracorporeal soft portion 140 and guides the lower bending wire 161*d* to the rotation drum 156.

The rotation drum 156 is supported by the support member 155 rotatably around the drum rotation shaft 156*r* extending in the longitudinal direction A. The rotation drum 156 includes a winding pulley 156*a* and a coupling portion 156*c*.

The winding pulley 156*a* pulls or sends out the upper bending wire 161*u* and the lower bending wire 161*d* by rotating around the drum rotation shaft 156*r*. When the winding pulley 156*a* rotates clockwise as seen from the distal end side A1 toward the proximal end side A2, the upper bending wire 161*u* is wound around the winding pulley 156*a* and pulled and the lower bending wire 161*d* is sent out from the winding pulley 156*a*. In contrast, when the winding pulley 156*a* rotates counterclockwise, the upper bending wire 161*u* is sent out from the winding pulley 156*a* and the lower bending wire 161*d* is wound around the winding pulley 156*a* and pulled. With this configuration, even if an advance/retreat amount of the upper bending wire 161*u* and the lower bending wire 161*d* is large, the pulled portion is compactly stored and does not take up space.

In the upper bending wire 161*u* and the lower bending wire 161*d*, a portion wound around the winding pulley 156*a* has a larger diameter than other portions. Therefore, the upper bending wire 161*u* and the lower bending wire 161*d* can be suitably prevented from being sandwiched between the winding pulley 156*a* and the support member 155. Also, elongation of the upper bending wire 161*u* and the lower bending wire 161*d* associated with traction or relaxation can be suitably prevented.

The upper bending wire 161*u* and the lower bending wire 161*d* may have a diameter of a wire of a portion passing through the extracorporeal soft portion 140 that is larger than a diameter of a wire of a portion passing through the insertion portion 110. Thereby, the insertion portion 110 inserted into the body can be thinned. Also, by increasing the diameter of the wire of the portion passing outside the body, the elongation of the upper bending wire 161*u* and the lower bending wire 161*d* is suppressed and controllability in the bending manipulation for the bending portion 112 is improved.

The coupling portion 156*c* is a disk member that rotates around the drum rotation shaft 156*r*. The coupling portion 156*c* is fixed to the proximal end of the winding pulley 156*a* and rotates integrally with the winding pulley 156*a*. The coupling portion 156*c* is exposed on the proximal end side A2 of the upper/lower bending wire attachment/detachment portion 151. Two mating convex portions 156*d* are formed on the surface of the proximal end side A2 of the coupling portion 156*c*. The two mating convex portions 156*d* are formed on both sides across the drum rotation shaft 156*r*.

The tension sensor 159 detects the tension of the upper bending wire 161*u* and the lower bending wire 161*d*. A detection result of the tension sensor 159 is acquired by the drive controller 260.

[Drive Device 200]

Figure 10:
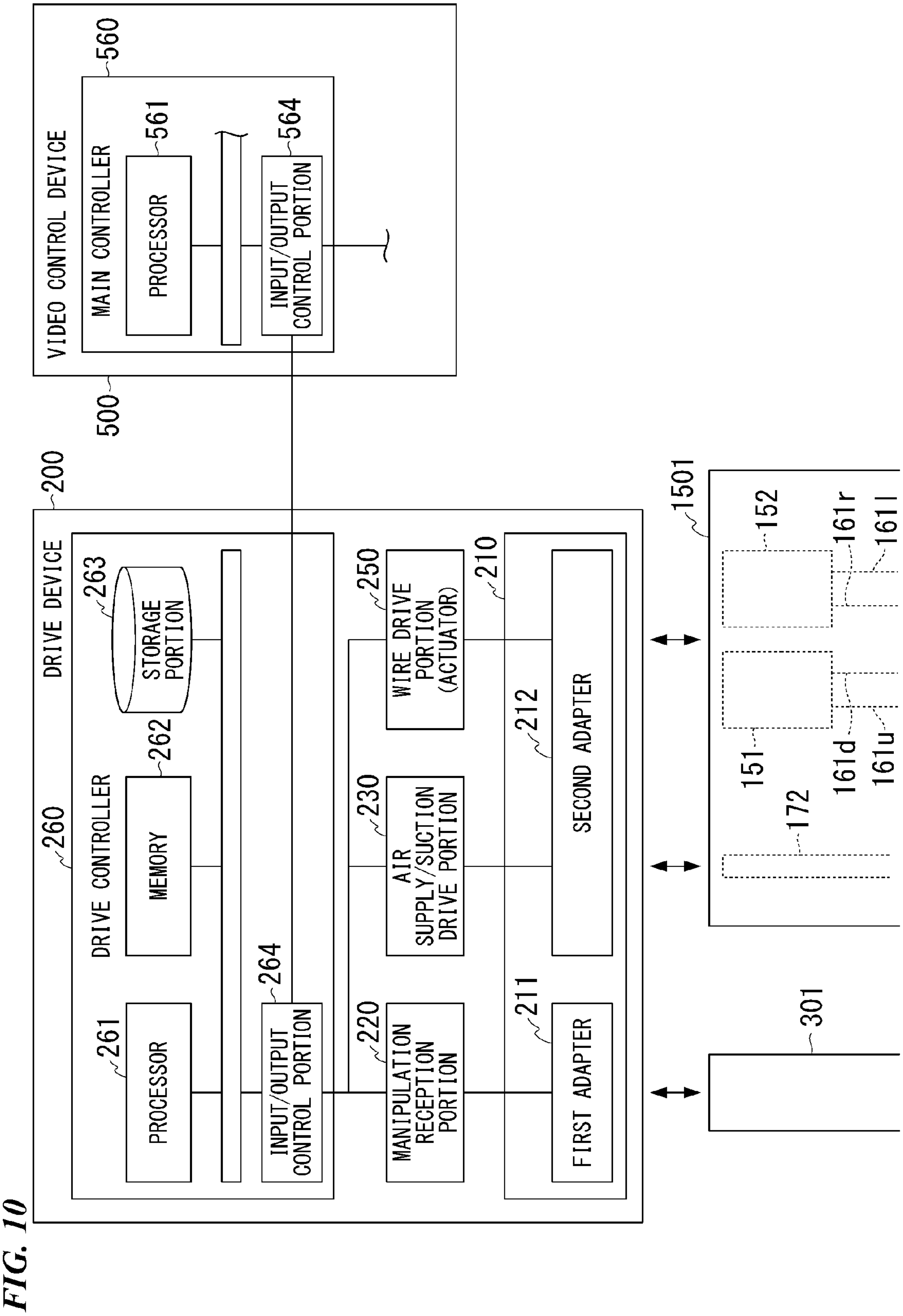
FIG. 10 is a functional block diagram of the drive device.

FIG. 10 is a functional block diagram of the drive device 200.

The drive device 200 includes an adapter 210, a manipulation reception portion 220, an air supply/suction drive portion 230, a wire drive portion (actuator) 250, and a drive controller 260.

The adapter 210 includes a first adapter 211 and a second adapter 212 as shown in FIG. 7. The first adapter 211 is an adapter to which the manipulation cable 301 is removably connected. The second adapter 212 is an adapter to which the first attachment/detachment portion 1501 of the endoscope 100 is removably connected.

The manipulation reception portion 220 receives a manipulation input from the controller 300 via the manipulation cable 301. When the controller 300 and the drive device 200 perform communication based on wireless communication instead of wired communication, the manipulation reception portion 220 has a known wireless reception module.

The air supply/suction drive portion 230 is connected to the air supply/suction tube 172 inserted into the internal path 101 of the endoscope 100. The air supply/suction drive portion 230 includes a pump and the like and supplies air to the air supply/suction tube 172. The air supply/suction drive portion 230 suctions air from the air supply/suction tube 172.

The wire drive portion (actuator) 250 drives the bending wire 160 by coupling with the upper/lower bending wire attachment/detachment portion 151 and the left/right bending wire attachment/detachment portion 152.

As shown in FIG. 7, the wire drive portion 250 includes an upper/lower bending wire drive portion (first actuator) 251 and a left/right bending wire drive portion (second actuator) 252.

The upper/lower bending wire drive portion 251 is a mechanism for driving wires (the upper bending wire 161*u* and the lower bending wire 161*d*) that bend the bending portion 112 in the UD direction by coupling with the upper/lower bending wire attachment/detachment portion 151.

The left/right bending wire drive portion 252 is a mechanism for driving wires (the left bending wire 161*l* and the right bending wire 161*r*) that bend the bending portion 112 in the LR direction by coupling with the left/right bending wire attachment/detachment portion 152.

Because the left/right bending wire drive portion 252 has a structure similar to that of the upper/lower bending wire drive portion 251, illustration and description thereof are omitted.

As shown in FIG. 8, the upper/lower bending wire drive portion 251 includes a support member 255, a bending wire drive portion 256, and an attachment/detachment sensor 259.

The bending wire drive portion 256 drives the upper bending wire 161*u* and the lower bending wire 161*d* by coupling with the rotation drum 156 of the upper/lower bending wire attachment/detachment portion 151. The bending wire drive portion 256 includes a shaft 256*a*, a motor portion 256*b*, a coupled portion 256*c*, a torque sensor 256*e*, and an elastic member 256*s*.

The shaft 256*a* is supported by the support member 255 that can rotate around the shaft rotation shaft 256*r* and can move forward and rearward in the longitudinal direction A. When the first attachment/detachment portion 1501 of the endoscope 100 is attached to the drive device 200, the shaft rotation shaft 256*r* coincides with the drum rotation shaft 156*r*.

The motor portion 256*b* includes a motor such as a DC motor, a motor driver configured to drive the motor, and a motor encoder. The motor rotates the shaft 256*a* around the shaft rotation shaft 256*r*. The motor driver is controlled by the drive controller 260.

The coupled portion 256*c* is a disk member that rotates around the shaft rotation shaft 256*r*. The coupled portion 256*c* is fixed to the distal end of the shaft 256*a* and rotates integrally with the shaft 256*a*. As shown in FIG. 8, the coupled portion 256*c* is exposed on the distal end side A1 of the upper/lower bending wire drive portion 251. Two mating concave portions 256*d* are formed on the surface of the distal end side A1 of the coupled portion 256*c*. The two mating concave portions 256*d* are formed on both sides across the shaft rotation shaft 256*r*.

As shown in FIG. 9, the mating convex portion 156*d* and the mating concave portion 256*d* are mated and the coupling portion 156*c* and the coupled portion 256*c* are coupled. As a result, the rotation of the shaft 256*a* by the motor portion 256*b* is delivered to the rotation drum 156. When the shaft 256*a* rotates clockwise as seen from the distal end side A1 toward the proximal end side A2, the upper bending wire 161*u* is pulled and the lower bending wire 161*d* is sent out. In contrast, when the shaft 256*a* rotates counterclockwise, the upper bending wire 161*u* is sent out and the lower bending wire 161*d* is pulled.

The torque sensor 256*e* detects rotational torque centered on the shaft rotation shaft 256*r* of the shaft 256*a*. A detection result of the torque sensor 256*e* is acquired by the drive controller 260.

The elastic member 256*s* is, for example, a compression spring, the distal end portion is in contact with the coupled portion 256*c*, and the proximal end portion is in contact with the support member 255. The elastic member 256*s* biases the coupled portion 256*c* to the distal end side A1. As shown in FIG. 9, when the coupling portion 156*c* is detached, the coupled portion 256*c* moves to the proximal end side A2 together with the shaft 256*a*.

As shown in FIG. 9, the attachment/detachment sensor 259 detects attachment/detachment with the upper/lower bending wire drive portion 251 in the upper/lower bending wire attachment/detachment portion 151 by detecting engagement and non-engagement with an attachment/detachment detection dog 155*a*. A detection result of the attachment/detachment sensor 259 is acquired by the drive controller 260.

The drive controller 260 controls the entire drive device 200. The drive controller 260 acquires the manipulation input received by the manipulation reception portion 220. The drive controller 260 controls the air supply/suction drive portion 230 and the wire drive portion 250 on the basis of the acquired manipulation input.

The drive controller 260 is a computer capable of executing a program and includes a processor 261, a memory 262, a storage portion 263 capable of storing programs and data, and an input/output control portion 264. The function of the drive controller 260 is implemented by the processor executing the program. At least some functions of the drive controller 260 may be implemented by a dedicated logic circuit.

Because the drive controller 260 controls a plurality of motors driving a plurality of bending wires 160 with high accuracy, it is desirable to have high calculation performance.

Also, the drive controller 260 may further have a component other than the processor 261, the memory 262, the storage portion 263, and the input/output control portion 264. For example, the drive controller 260 may further include an image calculation portion that performs a part or all of image processing or image recognition processing. By further including an image calculation portion, the drive controller 260 can perform specific image processing or image recognition processing at a high speed. The image calculation portion may be mounted on a separate hardware device connected by a communication circuit.

[Controller 300]

Figure 11:
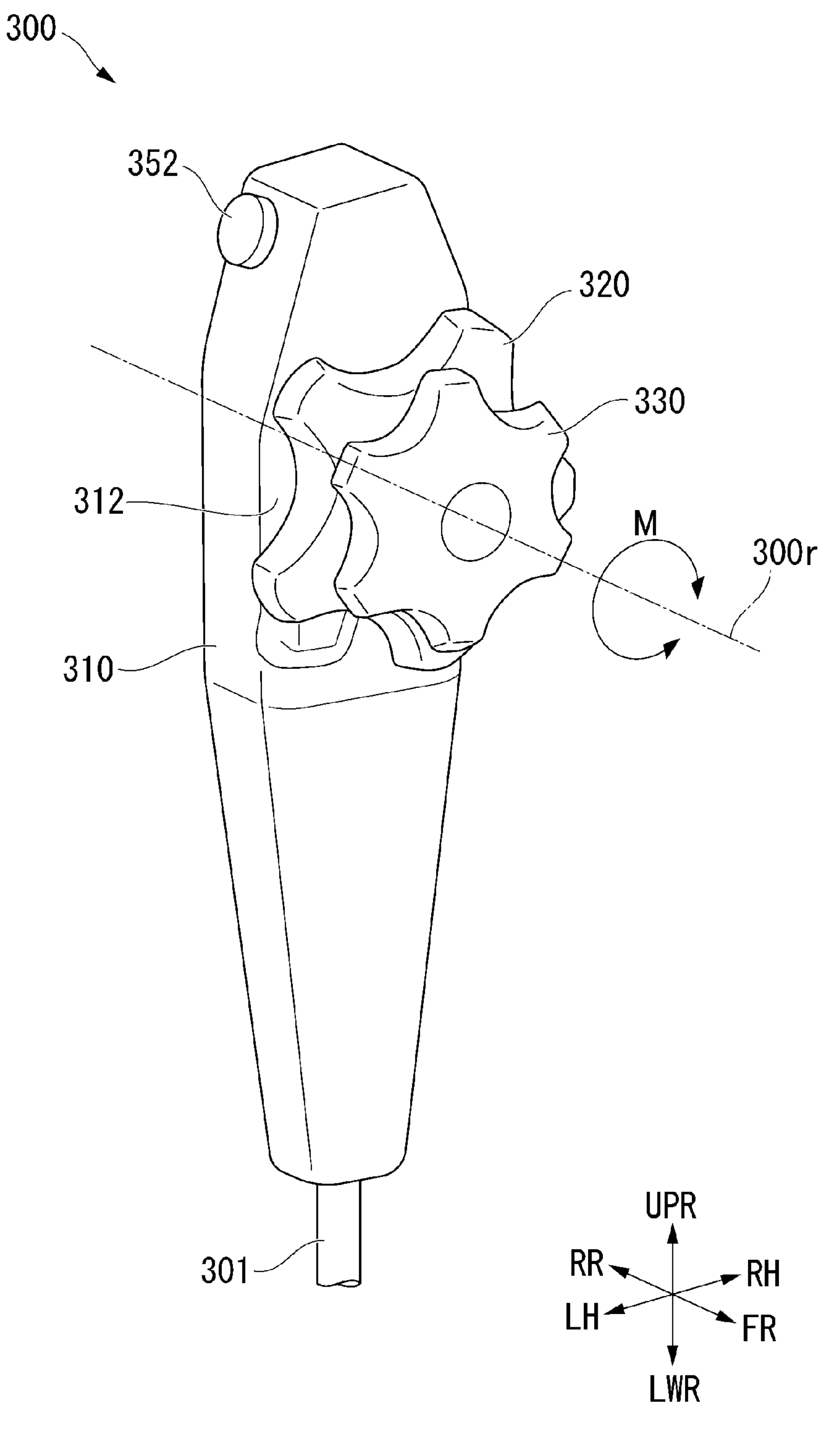
FIG. 11 is a perspective view of the controller of the medical manipulator system.
Figure 12:
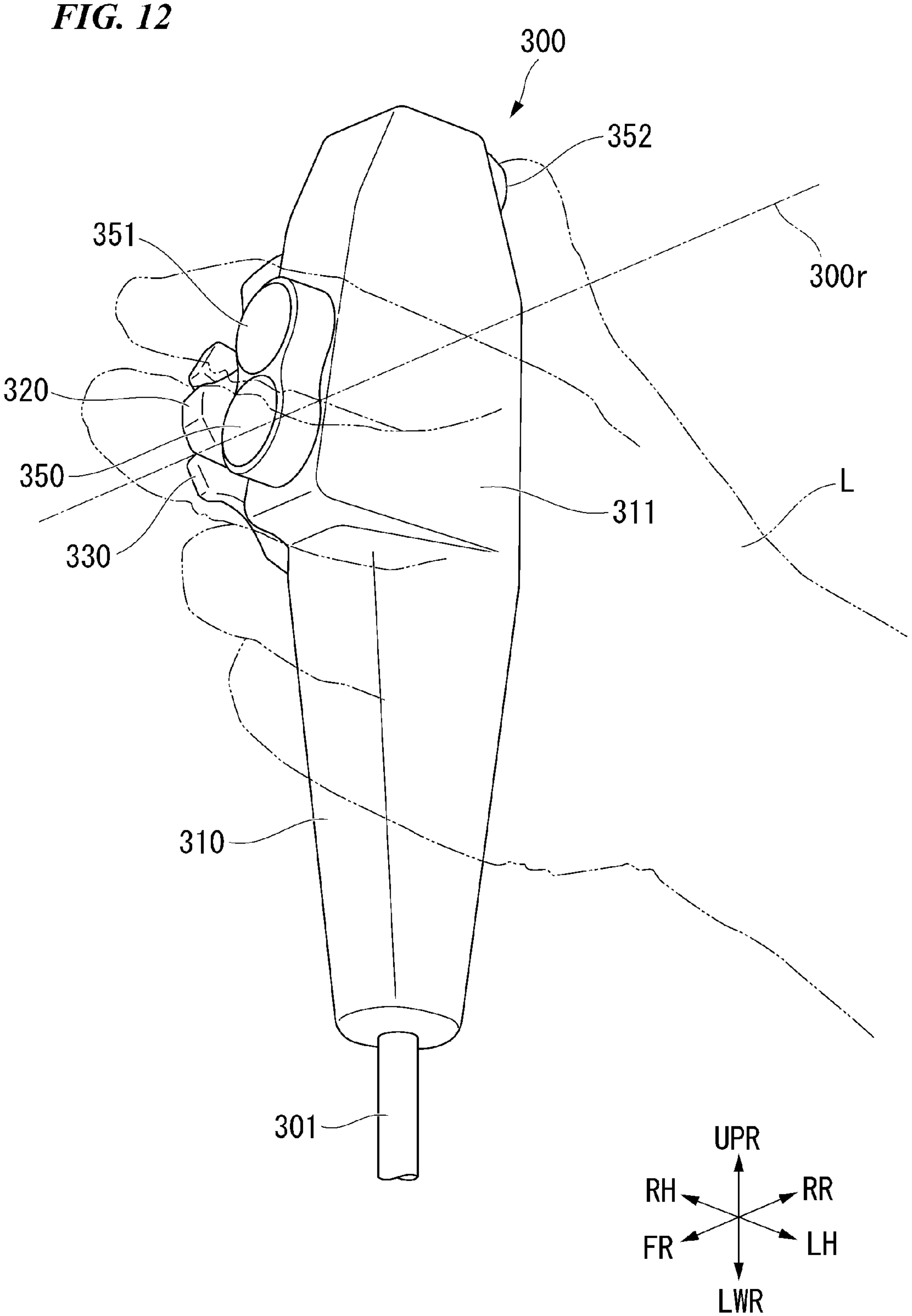
FIG. 12 is a perspective view of the controller seen from the rear.
Figure 13:
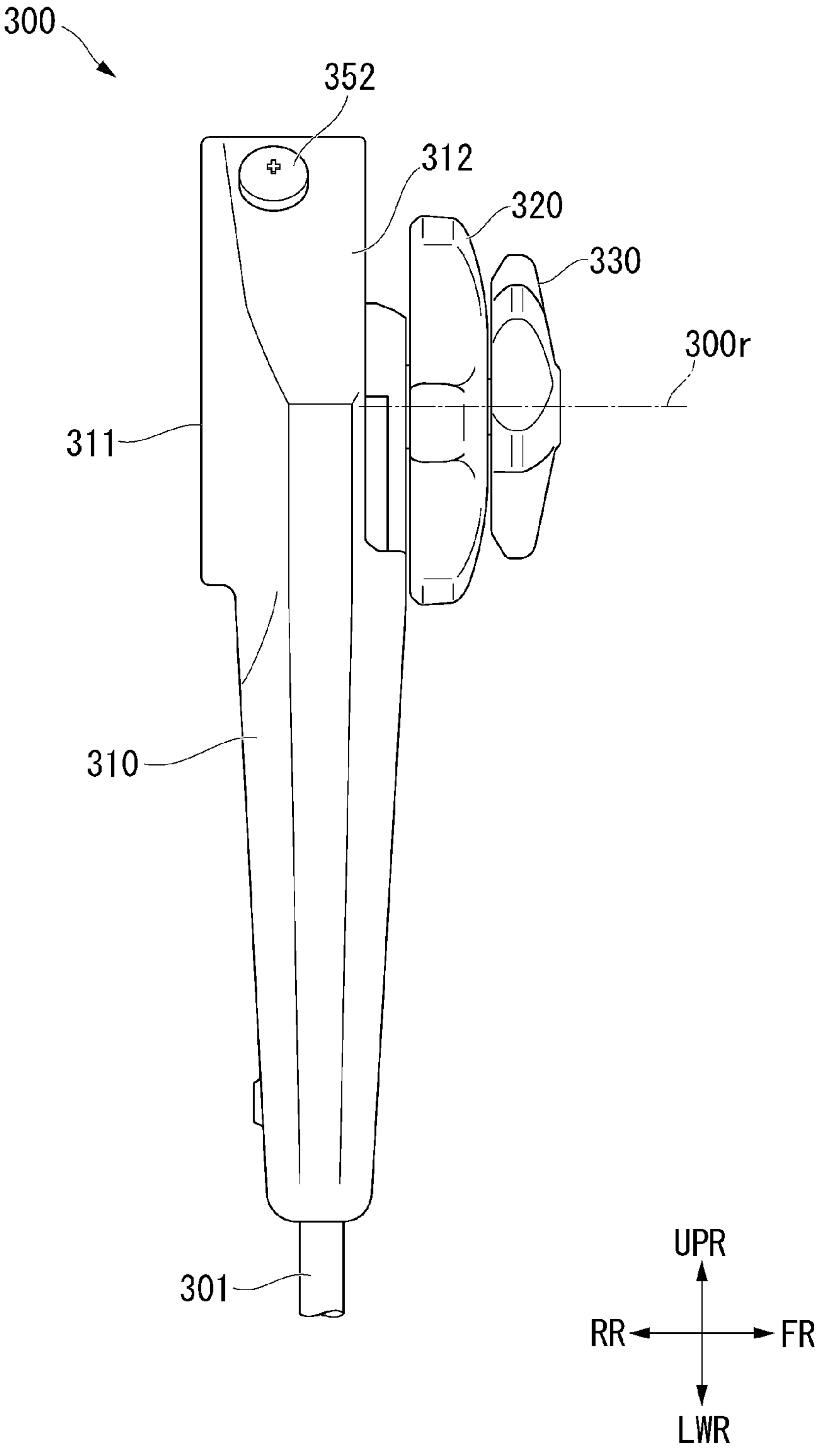
FIG. 13 is a side view of the controller.

FIG. 11 is a perspective view of the controller 300. FIG. 12 is a perspective view of the controller 300 seen from a back surface 311. FIG. 13 is a side view of the controller 300.

The controller 300 is a device in which a manipulation for driving the endoscope 100 is input. The input manipulation input is transmitted to the drive device 200 via the manipulation cable 301.

The controller 300 includes a manipulation portion body 310, a first angle knob 320, a second angle knob 330, an air supply button 350, a suction button 351, and various buttons 352.

The manipulation portion body 310 is formed in a substantially cylindrical shape that the physician S can hold with his or her left hand L. As shown in FIG. 12, in the manipulation portion body 310, the back surface 311 along which the palm of the left hand L of the physician S can be aligned is formed. The manipulation cable 301 is connected to the end portion of the manipulation portion body 310 in the longitudinal direction.

The first angle knob 320 and the second angle knob 330 are interfaces to which a bending manipulation to bend the bending portion 112 is input.

The first angle knob 320 and the second angle knob 330 are rotatably attached to the manipulation portion body 310. The first angle knob 320 and the second angle knob 330 are attached to a front surface 312 opposite the back surface 311. The first angle knob 320 and the second angle knob 330 rotate in a rotation direction M around the same rotation axis 300*r*.

The first angle knob 320 and the second angle knob 330 have an encoder (not shown) that detects a rotation angle, a rotation speed, and the like in the rotation manipulation input to the first angle knob 320 and the second angle knob 330. The detection result of the encoder is transmitted to the drive device 200.

In the following description, a direction of the rotation axis 300*r* of the first angle knob 320 and the second angle knob 330 is defined as a "forward/rearward direction" and a direction in which the first angle knob 320 and the second angle knob 330 are attached to the manipulation portion body 310 is defined as a "forward direction FR." A direction opposite the forward direction FR is defined as a "rearward direction RR." Also, a longitudinal direction of the manipulation portion body 310 is defined as an "upward/downward direction" and a direction in which the manipulation cable 301 is attached to the manipulation portion body 310 is defined as a "downward direction LWR." A direction opposite the downward direction LWR is defined as an "upward direction UPR." A right direction toward the rearward direction RR is defined as a "right direction RH." A direction opposite the right direction RH is defined as a "left direction LH." A direction toward the right direction RH or the left direction LH is defined as a "left/right direction."

In the present embodiment, the direction (the forward/rearward direction) of the rotation axis 300*r* of the first angle knob 320 and the second angle knob 330 is a direction substantially perpendicular to the back surface 311 of the manipulation portion body 310.

The air supply button 350 is attached to the manipulation portion body 310 in the upward direction UPR and is manipulated by the index finger or the middle finger of the left hand L as shown in FIG. 12. When the air supply button 350 is pushed, air is supplied from the opening 111*a* of the distal end portion 111 of the endoscope 100. The manipulation of the air supply button 350 is transmitted to the drive device 200. Here, the air supply button 350 may receive a manipulation for supplying a liquid such as water from the distal end portion 111 of the endoscope 100. When the air supply button 350 has a water supply function, for example, when the air supply button 350 (air supply/water supply button) is pushed, water is supplied from the opening 111*a* of the distal end portion 111 of the endoscope 100. At this time, for example, the drive device 200 has a water supply drive portion (not shown) including a pump or the like and the manipulation of the air supply button 350 is transmitted to the water supply drive portion, so that water is supplied from the distal end portion 111 of the endoscope 100.

When water is supplied from the opening 111*a* by manipulating the air supply button 350, for example, the endoscope 100 is connected to the above-described water supply drive portion and includes a water supply tube (not shown) in which a liquid such as water flows from the water supply drive portion. Also, at this time, the air supply/suction tube 172 may function as an air supply/water supply tube capable of supplying air and water. In this case, the air supply/suction drive portion 230 in the drive device 200 is preferably divided into an air supply drive portion that performs air supply and a suction drive portion that performs suction.

For example, the above-described air supply/water supply tube branches into a water supply tube and an air supply tube at the proximal end side A2 of the insertion portion 110. A liquid such as water flows from the water supply drive portion to the air supply/water supply tube via the water supply tube and air is sent from the above-described air supply drive portion to the air supply/water supply tube via the air supply tube.

At this time, the channel tube 171 may function as a suction tube capable of performing suction. In this case, the suction tube (the channel tube 171) is connected to the above-described suction drive portion and suction is performed from the opening 111*a* via the suction tube when the suction drive portion is driven. Also, on the proximal end side A2 of the insertion portion 110, the channel tube 171 branches into a portion connected to the forceps port 126 that is an insertion port of the treatment tool 400 and a portion connected to the suction drive portion.

That is, the tube that performs air supply and suction is not limited to an integrated tube (the air supply/suction tube 172). Air supply may be carried out by the above-described air supply tube and air suction may be carried out by the channel tube 171 (the suction tube). Also, the endoscope 100 may have the water supply tube that performs water supply at the proximal end side A2 of the insertion portion 110 and may have the air supply/water supply tube into which the air supply tube and the water supply tube merge and which can perform air supply and water supply at the insertion portion 110.

The suction button 351 is attached to the manipulation portion body 310 in the upward direction UPR and is manipulated by the index finger or the middle finger of the left hand L as shown in FIG. 12. When the suction button 351 is pushed, suction is performed from the opening 111*a* of the distal end portion 111 of the endoscope 100. The manipulation of the suction button 351 is transmitted to the drive device 200. Also, the suction performed from the opening 111*a* may be performed by the air supply/suction tube 172 capable of performing air supply and suction or may be performed by the channel tube 171 (the suction tube) as described above when the air supply and the suction are performed by different tubes.

The various buttons 352 are attached to the manipulation portion body 310 in the upward direction UPR and are manipulated by the thumb of the left hand L as shown in FIG. 12. Any functions can be assigned to the various buttons 352. For example, when the various buttons 352 are pushed, the bending portion 112 may be configured to switch the control to angle-free control for passively making bending with respect to an external force. Also, when there is no function to be assigned to the various buttons 352 and the various buttons 352 are not required, the controller 300 may not include the various buttons 352.

The drive controller 260 of the drive device 200 acquires the manipulation input transmitted by the controller 300 and controls the air supply/suction drive portion 230 and the wire drive portion 250.

The drive controller 260 controls the upper/lower bending wire drive portion 251 on the basis of the rotation manipulation input to the first angle knob 320 so that wires (the upper bending wire 161*u* and the lower bending wire 161*d*) that bend the bending portion 112 in the UD direction are driven. Also, the drive controller 260 controls the left/right bending wire drive portion 252 on the basis of the rotation manipulation input to the second angle knob 330 so that wires (the left bending wire 161*l* and the right bending wire 161*r*) that bend the bending portion 112 in the LR direction are driven.

Figure 14:
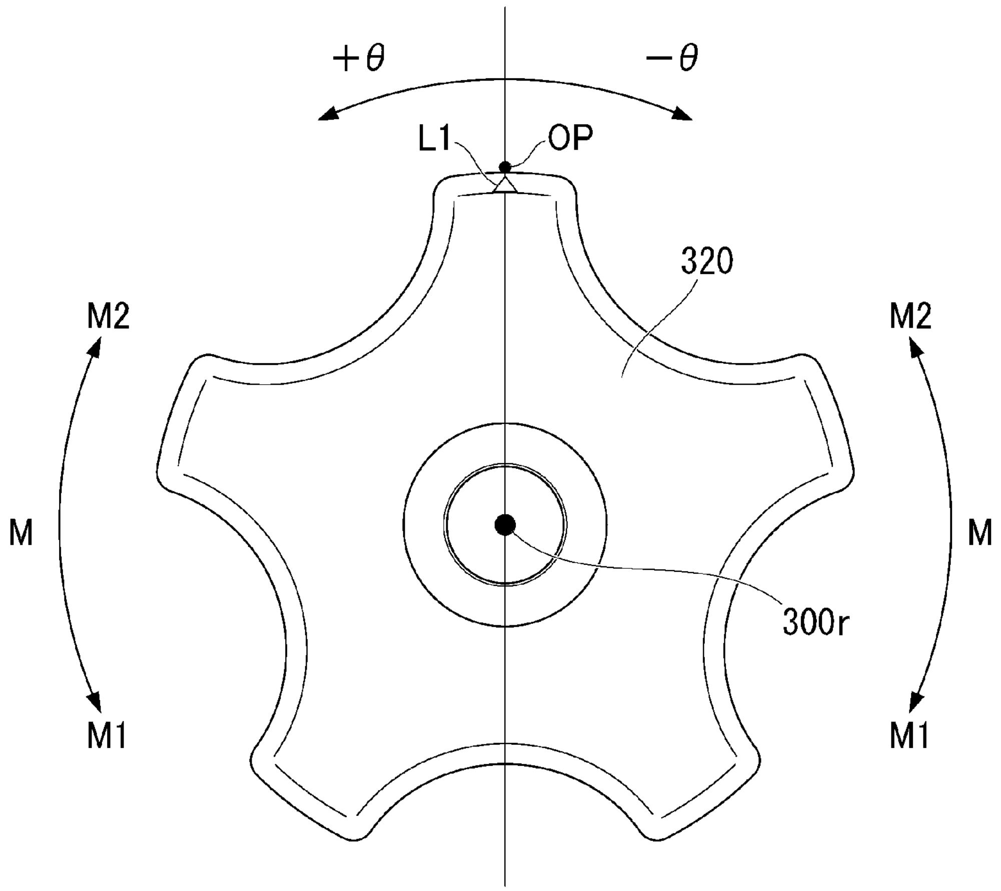
FIG. 14 is a front view showing a first angle knob in the controller.

FIG. 14 is a front view of the first angle knob 320 as seen from the forward direction FR. As shown in FIG. 14, an initial position of the first angle knob 320 is a position where the origin OP and the reference point L1 at the first angle knob 320 are aligned. The first angle knob 320 can be rotated with the rotation axis 300*r* as the rotation center and is rotated in a direction in which the reference point L1 is away from the origin OP (a first direction M1) and a direction in which the reference point L1 returns to the origin OP (a second direction M2) so that a bending manipulation is input.

Figure 15:
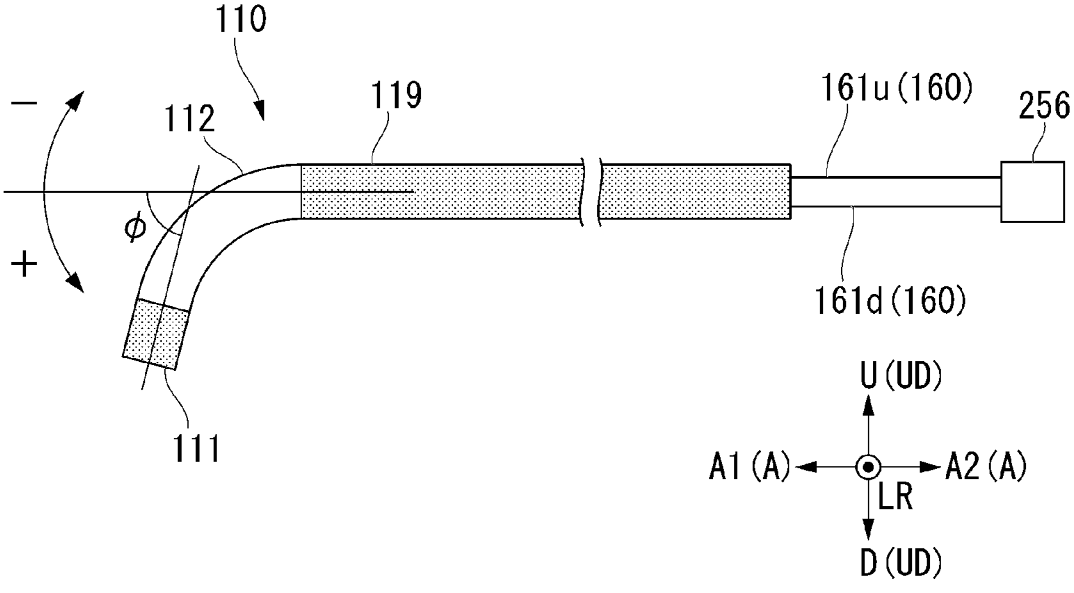
FIG. 15 is a diagram showing the bending portion that is bent.

FIG. 15 is a diagram showing the bending portion 112 that is bent. A bending amount of the bending portion 112 is, for example, a bending angle of the bending portion that is bent, curvature of bending of the bending portion that is bent, a traction amount and a relaxation amount of a wire that inputs motive power for the bending of the bending portion, or a control amount of the drive portion (the motor, the actuator, or the like) that generates a driving force for the bending of the bending portion. In the following description, a case where a bending amount of the bending portion 112 is a bending angle of the bending portion 112 will be described. A bending angle ϕ shown in FIG. 15 indicates an angular displacement amount (the displacement of the bending amount) from the reference angle (the reference bending amount) at the bending portion 112. Here, the reference angle is an angle to be taken by the bending portion 112 when the first angle knob 320 is located at the origin OP (the initial position). The reference angle in the present embodiment is an angle of a case where the bending portion 112 is not bent and has a straight shape.

The bending portion 112 bends in a +ϕ direction shown in FIG. 15 by rotating the first angle knob 320 in a +θ direction shown in FIG. 14. The bending portion 112 bends in a −ϕ direction shown in FIG. 15 by rotating the first angle knob 320 in a −θ direction shown in FIG. 14.

Like the first angle knob 320, the second angle knob 330 is rotated in a direction in which the reference point L1 is away from the origin OP (the first direction M1) using the rotation axis 300*r* as the rotation center and a direction in which the reference point L1 returns to the origin OP (the second direction M2) so that a bending manipulation is input. In the present embodiment, the initial position of the second angle knob 330 is a position where the origin OP and the reference point (not shown) at the second angle knob 330 are aligned. The origin in the first angle knob 320 and the origin in the second angle knob 330 may not be located at the same position.

In the controller 300, the interface to which the bending manipulation of bending the bending portion 112 is input may be a lever, a knob, or a dial. For example, the interface may be a lever-type knob or a sliding knob. The controller 300 has a sensor (for example, an encoder) that matches the form of the interface of the controller 300 and detects movement amounts (for example, rotation angles) and movement directions of interfaces of the controller 300 (for example, the first angle knob 320 and the second angle knob 330) from the origin OP to transmit the detected movement amounts and the detected movement directions to the drive device 200.

When the upward direction UPR of the controller 300 is associated with the distal end side A1 of the endoscope 100 in the longitudinal direction A, the rotation direction of the first angle knob 320 or the second angle knob 330 coincides with the bending direction of the bending portion 112 of the distal end of the endoscope 100. Therefore, it becomes an intuitive corresponding relationship for the physician S and suitable manipulability may be provided.

Because the controller 300 does not include a drive mechanism for driving the bending portion 112 of the endoscope 100, it is small and lightweight. The first angle knob 320, the second angle knob 330, the air supply button 350, the suction button 351, and the various buttons 352 are arranged at a position where the physician S can sufficiently perform a manipulation with only his or her left hand L. Therefore, as shown in FIG. 2, the physician S performs an easy manipulation by holding the controller 300 only with his or her left hand L.

[Video Control Device 500]

Figure 16:
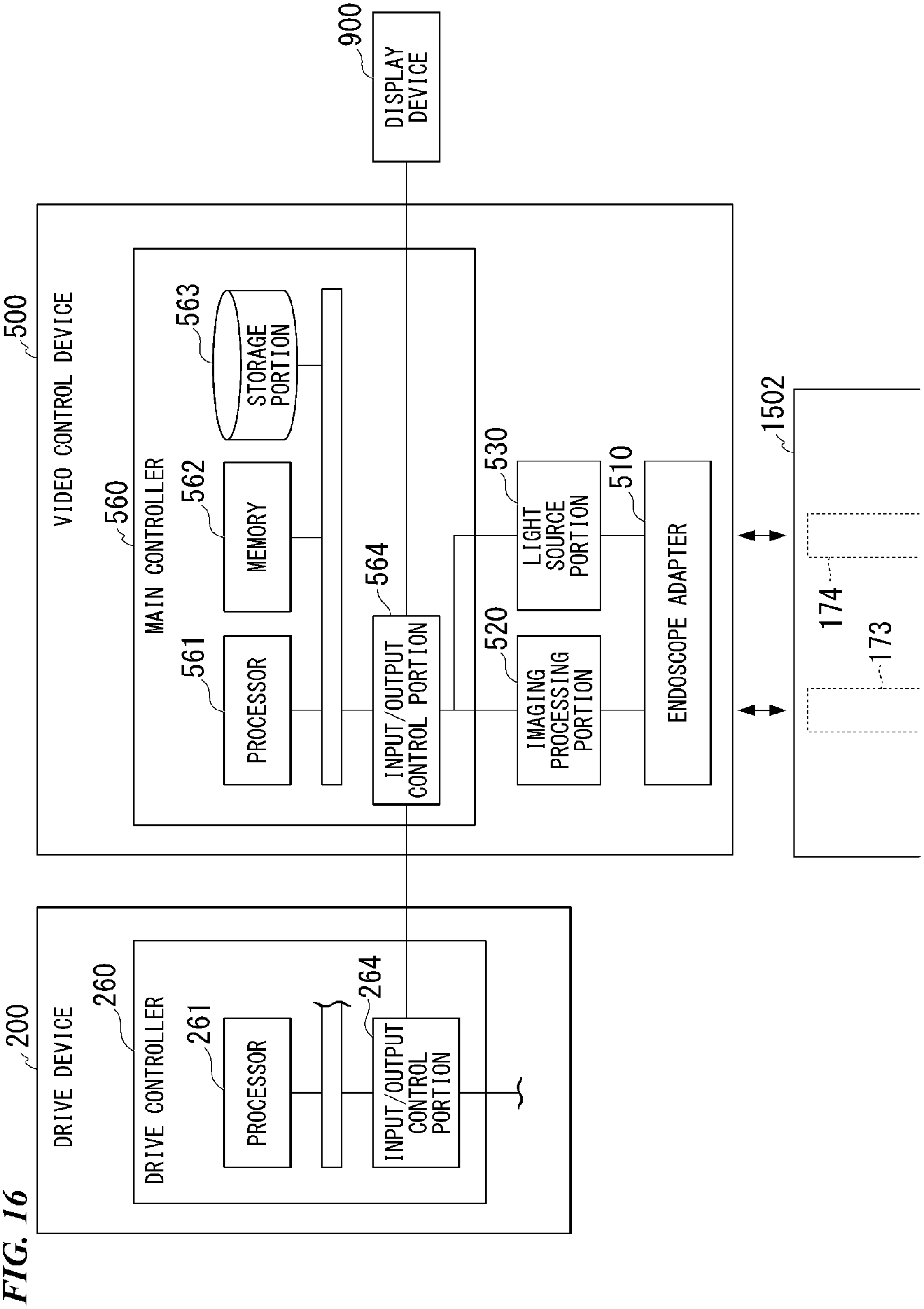
FIG. 16 is a functional block diagram of the video control device of the medical manipulator system.

FIG. 16 is a functional block diagram of the video control device 500.

The video control device 500 controls a motorized endoscope system 1000. The video control device 500 includes a third adapter 510, an imaging processing portion 520, a light source portion 530, and a main controller 560.

The third adapter 510 is an adapter to which the second attachment/detachment portion 1502 of the endoscope 100 is removably attached.

The imaging processing portion 520 converts an imaging signal acquired from the imaging portion 111*c* of the distal end portion 111 via the imaging cable 173 into a captured image.

The light source portion 530 generates illumination light applied to an imaging target. The illumination light generated by the light source portion 530 is guided to the illumination portion 111*b* of the distal end portion 111 via the light guide 174.

The main controller 560 is a computer capable of executing a program and includes a processor 561, a memory 562, a storage portion 563 capable of storing programs and data, and an input/output control portion 564. The function of the main controller 560 is implemented by the processor 561 executing a program. At least some functions of the main controller 560 may be implemented by a dedicated logic circuit.

The main controller 560 includes the processor 561, the memory 562 from which a program can be read, the storage portion 563, and the input/output control portion 564.

The storage portion 563 is a non-volatile recording medium that stores the above-described program and necessary data. The storage portion 563 includes, for example, a ROM, a hard disk, and the like. The program recorded in the storage portion 563 is read into the memory 562 and executed by the processor 561.

The input/output control portion 564 is connected to the imaging processing portion 520, the light source portion 530, the drive device 200, the display device 900, an input device (not shown), and a network device (not shown). The input/output control portion 564 performs the transmission/reception of data or the transmission/reception of a control signal to/from the connected device on the basis of control of the processor 561.

The main controller 560 can perform image processing on the captured image acquired by the imaging processing portion 520. The main controller 560 can generate a GUI image or a CG image for the purpose of providing information to the physician S. The main controller 560 can cause the display device 900 to display the captured image, the GUI image, or the CG image.

The main controller 560 is not limited to an integrated hardware device. For example, the main controller 560 may be configured by partially separating it as a separate hardware device and connecting the separated hardware device through a communication circuit. For example, the main controller 560 may be a cloud system that connects the storage portion 563, which is separated, through a communication circuit.

The main controller 560 may further have a component other than the processor 561, the memory 562, the storage portion 563, and the input/output control portion 564 shown in FIG. 16. For example, the main controller 560 may further include an image calculation portion that performs a part or all of the image processing or image recognition processing performed by the processor 561. By further including the image calculation portion, the main controller 560 can perform specific image processing and image recognition processing at a high speed. The image calculation portion may be mounted on a separate hardware device connected by a communication circuit.

[Operation of Motorized Endoscope System 1000]

Next, an operation of the motorized endoscope system 1000 of the present embodiment will be described. Specifically, a procedure for observing and treating an affected area formed in a canal wall in the large intestine using the motorized endoscope system 1000 will be described.

Figure 17:
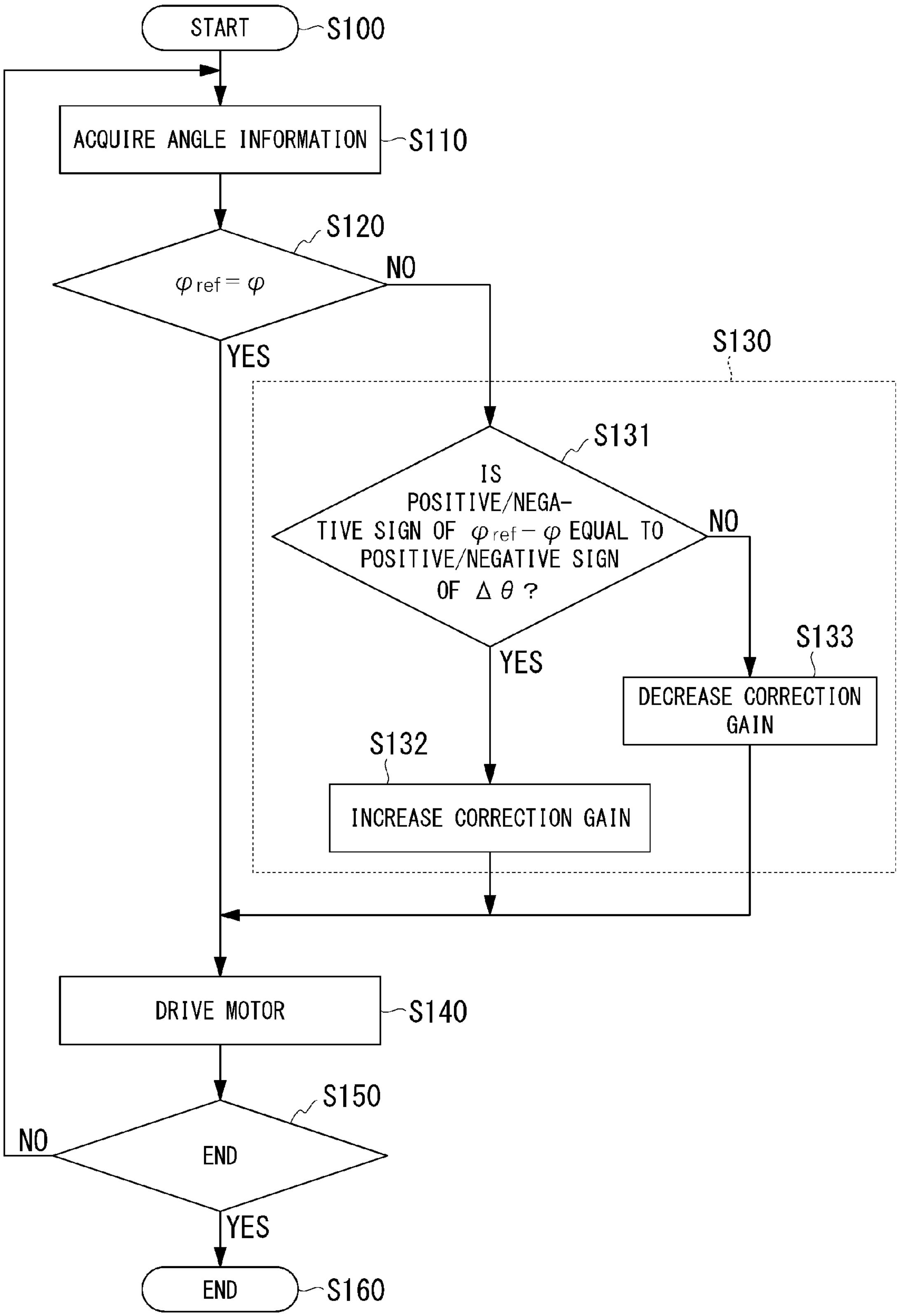
FIG. 17 is a flowchart showing control of the medical manipulator system in the drive device.

In the following description, the description will be given with reference to the control flowchart of the drive controller 260 of the control device 600 shown in FIG. 17. When the control device 600 is activated, the drive controller 260 performs initialization (step S100). Subsequently, the drive controller 260 (mainly the processor 261) executes step S110.

Figure 18:
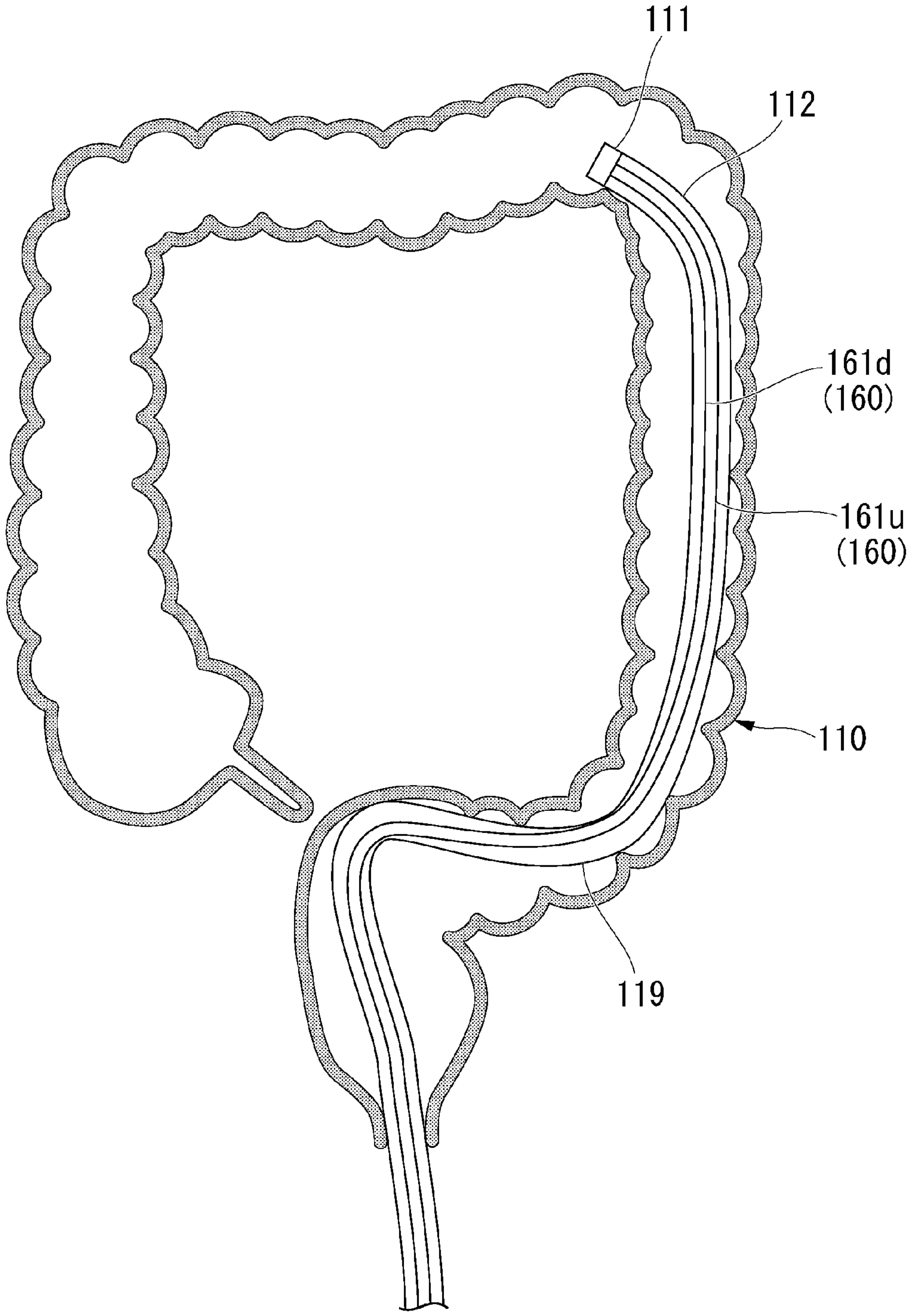
FIG. 18 is a diagram showing the insertion portion inserted into the large intestine.

FIG. 18 is a diagram showing the insertion portion 110 inserted into the large intestine.

The physician S inserts the insertion portion 110 of the endoscope 100 into the large intestine from the anus of the patient P. While observing the captured image displayed on the display device 900, the physician S moves the insertion portion 110 while manipulating the intracorporeal soft portion 119 with his or her right hand R and brings the distal end portion 111 closer to the affected area. Also, the physician S manipulates the controller 300 with his or her left hand L to input a bending manipulation for the bending portion 112.

<Step S110>

The drive controller 260 performs bending control on the bending portion 112 on the basis of the received bending manipulation and controls the wire drive portion (actuator) 250 to bend the bending wire 160.

In the following description, control in the drive controller 260 when a bending manipulation is input to the first angle knob 320 will be described. The drive controller 260 performs similar control for the bending manipulation input to the second angle knob 330.

In step S110, the drive controller 260 acquires an angular displacement amount from a reference angle at the bending portion 112.

The drive controller 260 acquires a first angle $\phi$ (a first bending amount) calculated on the basis of a rotation angle (a driving amount) of the motor portion **256*b* detected by the motor encoder. An acquisition means for acquiring the first angle $\phi$ is not limited to this and the drive controller 260, for example, may acquire an angle calculated on the basis of the strain detected by a strain sensor arranged on the outer sheath 118 in the bending portion 112**.

Also, the drive controller 260 acquires a second angle $\phi_{ref}$ (a second bending amount), which is an angular displacement amount from the reference angle in the bending portion 112 calculated on the basis of a rotation angle $\theta$ (a movement amount) of the first angle knob 320 in step S110.

As shown in Eq. (1), the second angle $\phi_{ref}$ is calculated by the processor 261 of the drive controller 260 on the basis of the rotation angle $\theta$ of the first angle knob 320 detected by the encoder provided in the controller 300 and a conversion factor $k_{nob}$. The conversion factor $k_{nob}$ can be appropriately set to any value according to the configuration of the motorized endoscope system 1000 or the like.

$$\phi_{ref} = \theta \times k_{nob} \qquad \text{Eq. (1)}$$

The drive controller 260 subsequently performs step S120.

<Step S120>

In step S120, the drive controller 260 compares the first angle $\phi$ and the second angle $\phi_{ref}$ acquired in step S110. When the first angle $\phi$ and the second angle $\phi_{ref}$ acquired in step S110 are different angles, the drive controller 260 subsequently executes step S130.

<Step S130>

When the first angle $\phi$ and the second angle $\phi_{ref}$ compared in step S120 are different angles, the actual bending angle and the bending angle in a gripping process of the physician S are likely to be different from each other in the bending angle in the bending portion 112. Here, the actual bending angle indicates the first angle $\phi$ calculated on the basis of the rotation angle of the motor portion **256*b***.

For example, when angle-free control in which the bending portion 112 is passively bent with respect to an external force has been performed, the first angle knob 320 does not follow the bending operation of the bending portion 112 bent by the external force because the controller 300 does not have a drive mechanism for driving the bending portion 112. Therefore, when the bending manipulation has been input to the controller 300, the actual bending angle and the bending angle indicated by the controller 300 are different from each other and the manipulability of the motorized endoscope system 1000 is likely to deteriorate.

The drive controller 260 controls the wire drive portion 250 so that a difference between the first angle $\phi$ and the second angle $\phi_{ref}$ is eliminated by increasing or decreasing the ratio of the second angle $\phi_{ref}$ to the rotation angle $\theta$ of the first angle knob 320. The calculation of the ratio of the second angle $\phi_{ref}$ to the rotation angle $\theta$ of the first angle knob 320 will be described below.

<Step S131>

The drive controller 260 first executes step S131 in step S130. The drive controller 260 compares sign($\phi_{ref}-\phi$) with sign($\Delta\theta$) in step S131.

Here, sign(x) is a sign function of returning a number corresponding to the sign (positive or negative) of the variable x. When x is positive, sign(x) returns 1. When x is 0, sign(x) returns 0. When x is negative, sign(x) returns −1.

Also, $\Delta\theta$ indicates an angular displacement amount of the first angle knob 320 input according to the bending manipulation. That is, in step S131, the drive controller 260 compares the positive/negative sign of a value obtained by subtracting the first angle $\phi$ from the second angle $\phi_{ref}$ with the positive/negative sign of an angular displacement amount of the first angle knob 320.

When sign($\phi_{ref}-\phi$) and sign($\Delta\theta$) are equal, the drive controller 260 executes step S132.

<Step S132>

In step S132, the drive controller 260 acquires a ratio of the second angle $\phi_{ref}$ to the rotation angle $\theta$ of the first angle knob 320 (a correction gain s) according to Eq. (2).

$$s = 1 + \mathrm{abs}(\phi_{ref} - \phi) \times k_s \qquad \text{Eq. (2)}$$

Here, $k_s$ is a correction factor stored in advance in the storage portion 263. The processor 261 of the drive controller 260 acquires the correction factor $k_s$ from the storage portion 263 and calculates the ratio according to Eq. (2). Also, abs(y) indicates an absolute value of a variable y.

When an absolute value of the first angle $\phi$ is smaller than an absolute value of the second angle $\phi_{ref}$ and the first angle knob 320 is rotated in a direction away from the origin OP (the first direction M1), sign($\phi_{ref}-\phi$) and sign($\Delta\theta$) are equal.

In this case, the actual bending angle (the first angle $\phi$) of the bending portion 112 is closer to the reference angle than the bending angle (the second angle $\phi_{ref}$) indicated by the controller 300. Therefore, even if the physician S rotates the first angle knob 320 in the first direction M1 so that the bending angle is farther away from the reference angle, the bending portion 112 does not bend to the bending angle assumed by the physician S. At this time, the drive controller 260 uses Eq. (2) to increase the ratio of the second angle $\phi_{ref}$ to the rotation angle $\theta$ of the first angle knob 320. When the ratio is increased, the bending portion 112 can be bent so that the difference between the first angle $\phi$ and the second angle $\phi_{ref}$ is eliminated.

Also, when the absolute value of the first angle $\phi$ is larger than the absolute value of the second angle ref and the first angle knob 320 is rotated in the direction returning to the origin OP (the second direction M2), sign($\phi_{ref}$−$\phi$) and sign ($\Delta\theta$) are equal.

In this case, the actual bending angle (the first angle $\phi$) of the bending portion 112 is further away from the reference angle than the bending angle (the second angle $\phi_{ref}$) indicated by the controller 300. Therefore, even if the physician S rotates the first angle knob 320 in the second direction M2 so that the bending angle approaches the reference angle, the bending portion 112 does not return to the bending angle assumed by the physician S. At this time, the drive controller 260 uses Eq. (2) to increase the ratio of the second angle $\phi_{ref}$ to the rotation angle $\theta$ of the first angle knob 320. When the ratio is increased, the bending portion 112 can be bent so that the difference between the first angle $\phi$ and the second angle $\phi_{ref}$ is eliminated.

Subsequently, in step S131, a case where sign($\phi_{ref}$−$\phi$) and sign($\Delta\theta$) are different will be described. The drive controller 260 executes step S133 when sign($\phi_{ref}$−$\phi$) and sign($\Delta\theta$) are different in step S131.

<Step S133>

In step S133, the drive controller 260 acquires the ratio of the second angle $\phi_{ref}$ to the rotation angle $\theta$ of the first angle knob 320 (the correction gain s) according to Eq. (3).

$$s = 1 - \mathrm{abs}(\phi_{ref} - \phi) \times k_s \qquad \text{Eq. (3)}$$

When the absolute value of the first angle $\phi$ is smaller than the absolute value of the second angle $\phi_{ref}$ and the first angle knob 320 is rotated in the direction returning to the origin OP (the second direction M2), sign($\phi_{ref}$−$\phi$) and sign($\Delta\theta$) are different.

In this case, the actual bending angle (the first angle $\phi$) of the bending portion 112 is closer to the reference angle than the bending angle (the second angle $\phi_{ref}$) indicated by the controller 300. Therefore, when the physician S rotates the first angle knob 320 in the second direction M2 so that the bending angle approaches the reference angle, the bending portion 112 returns to an angle closer to the reference angle than the bending angle assumed by the physician S. At this time, the drive controller 260 uses Eq. (3) to reduce the ratio of the second angle $\phi_{ref}$ to the rotation angle $\theta$ of the first angle knob 320. When the ratio is decreased, the bending portion 112 can be bent so that the difference between the first angle $\phi$ and the second angle $\phi_{ref}$ is eliminated.

Also, when the absolute value of the first angle $\phi$ is larger than the absolute value of the second angle $\phi_{ref}$ and the first angle knob 320 is rotated in the direction away from the origin OP (the first direction M1), sign($\phi_{ref}$−$\phi$) and sign($\Delta\theta$) are different.

In this case, the actual bending angle (the first angle $\phi$) of the bending portion 112 is further away from the reference angle (the second angle $\phi_{ref}$) indicated by the controller 300. Therefore, when the physician S rotates the first angle knob 320 in the first direction M1 so that the bending angle is further away from the reference angle, the bending portion 112 is bent to an angle further away from the reference angle than the bending angle assumed by the physician S. At this time, the drive controller 260 uses Eq. (3) to reduce the ratio of the second angle $\phi_{ref}$ to the rotation angle $\theta$ of the first angle knob 320. When the ratio is decreased, the bending portion 112 can be bent so that the difference between the first angle $\phi$ and the second angle $\phi_{ref}$ is eliminated.

Also, in the processing of step S130, a combination of different positive/negative signs of the first angle $\phi$ and the second angle $\phi_{ref}$ is excluded.

<Step S140>

After the ratio (the correction gain s) is calculated in step S130, the drive controller 260 drives the wire drive portion 250 (the actuator) on the basis of the calculated ratio (step S140). Subsequently, the drive controller 260 executes step S150.

<Step S150>

When a bending manipulation is not input to the first angle knob 320 in step S150, the drive controller 260 moves to step S160 and ends control. When a bending manipulation is input to the first angle knob 320, the process returns to step S110 and continues control.

Although a control flow when the first angle $\phi$ and the second angle $\phi_{ref}$ are different in step S120 has been described, the drive controller 260 executes step S140 and causes the wire drive portion 250 (the actuator) to be driven on the basis of the rotation angle $\theta$ of the first angle knob 320 when the first angle $\phi$ and the second angle $\phi_{ref}$ are equal in step S120. At this time, the drive controller 260 may cause the wire drive portion 250 to be driven using the ratio stored in advance in the storage portion 263 in the ratio of the second angle $\phi_{ref}$ to the rotation angle $\theta$.

Also, the drive controller 260 may control the wire drive portion 250 so that the bending portion 112 is bent to the maximum bending angle when the first angle knob 320 rotates to a rotation limit.

Here, the rotation limit of the first angle knob 320 indicates a position (an angle) in which the first angle knob 320 can only rotate up to the angle due to an abutting structure or the like. For example, in the first angle knob 320 shown in FIG. 14, the first angle knob 320 has the abutting structure that regulates the rotation angle of the first angle knob 320. When the first angle knob 320 is regulated by the abutting structure and the rotation angle $\theta$ can only rotate to the position of 150°, a position where the rotation angle $\theta$ is 150° is set as the rotation limit of the first angle knob 320.

Also, the maximum bending angle of the bending portion 112 is a maximum angle at which the bending portion 112 is bendable, and is, for example, any angle set in advance. The maximum bending angle of the bending portion 112 is, for example, the angle to be taken by the bending portion 112 when the first angle knob 320 is rotated to the rotation limit. Also, the maximum bending angle may be set according to a material, a structure, or the like of the bending portion 112.

The physician S rotates the first angle knob 320 to the rotation limit and makes the first angle knob 320 stationary at the rotation limit position. The drive controller 260 controls the wire drive portion 250 so that the bending portion 112 continues to bend until it bends to the maximum bending angle when the first angle knob 320 is located at the rotation limit. The bending portion 112 bends to the maximum bending angle and stops the bending operation.

For example, when the ratio of the second angle $\phi_{ref}$ to the rotation angle θ of the first angle knob 320 (the correction gain s) is less than 1, even if the first angle knob 320 is rotated to the rotation limit, the bending portion 112 is bent only to an angle smaller than the maximum bending angle.

When the first angle knob 320 rotates to the rotation limit, the bending portion 112 can be bent to the maximum bending angle and manipulability can be improved even if the ratio of the second angle $\phi_{ref}$ to the rotation angle θ of the first angle knob 320 (the correction gain s) is less than 1 by controlling the wire drive portion 250 so that the bending portion 112 is continuously bent until it bends to the maximum bending angle.

According to the motorized endoscope system 1000 according to the present embodiment, when the first angle ϕ, which is the angular displacement amount of the bending portion 112 calculated on the basis of the driving amount of the wire drive portion 250, is different from the second angle $\phi_{ref}$, which is the angular displacement amount of the bending portion 112 calculated on the basis of the movement amount (40) of the first angle knob 320 or the second angle knob 330, the wire drive portion 250 can be controlled so that the difference between the first angle ϕ and the second angle $\phi_{ref}$ is eliminated. As a result, the motorized endoscope system 1000 with improved manipulability can be provided.

Although the first embodiment of the present invention has been described above in detail with reference to the drawings, the specific configuration is not limited to the first embodiment and design changes and the like are also included without departing from the scope and spirit of the present invention. Also, the components shown in the above-described embodiments and modified examples can be appropriately combined and configured.

In the above-described embodiment, the physician S manipulates the controller 300 with his or her left hand L while manipulating the endoscope 100 with his or her right hand R. However, the usage mode of the motorized endoscope system 1000 is not limited to this. The physician S may manipulate the controller 300 with his or her right hand R while manipulating the endoscope 100 with his or her left hand L. In this case, the controller 300 is optimized so that a manipulation is easily performed with his or her right hand R.

In the above-described embodiment, the endoscope 100 has the bending portion 112 that is bent. However, aspects of the endoscope 100 are not limited to this. The endoscope 100 may have a bending function (a multistage bending function) in which the first bending portion and the second bending portion are bent in two stages. In this case, the controller may have a changeover switch that switches the bending manipulation of the first bending portion or the second bending portion. Also, the drive device may control the actuator so that a difference between an angular displacement amount of each bending portion calculated on the basis of the driving amount of the actuator and an angular displacement amount of each bending portion calculated on the basis of the angle of the first angle knob or the second angle knob is eliminated with respect to the first bending portion and the second bending portion.

Figure 19:
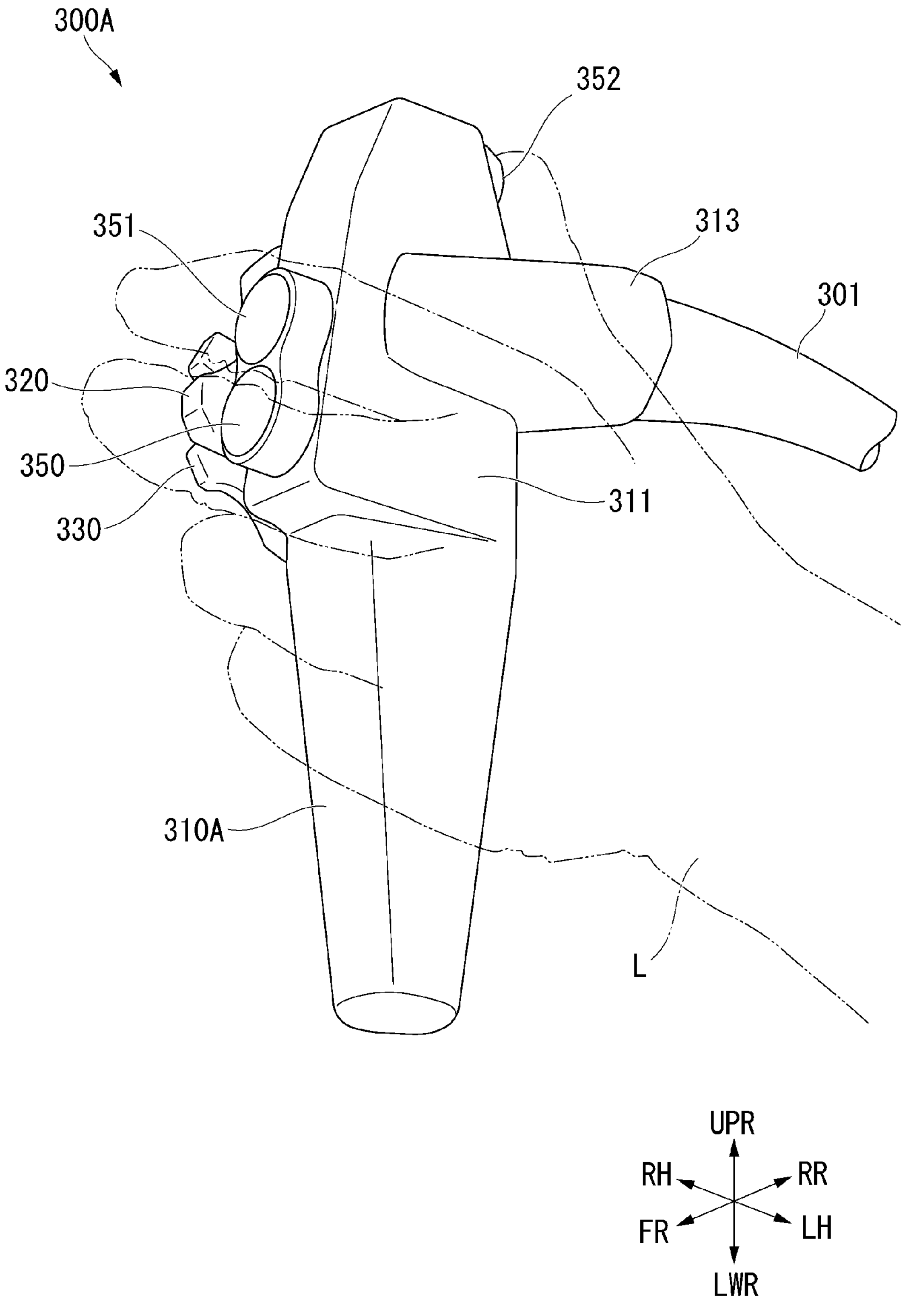
FIG. 19 is a perspective view of a modified example of the controller.

In the above-described embodiment, the manipulation cable 301 is attached to the end portion of the manipulation portion body 310 in the longitudinal direction. However, a connection position of the manipulation cable 301 in the manipulation portion body 310 is not limited to this. FIG. 19 is a perspective view of the controller 300A, which is a modified example of the controller 300. The controller 300A includes a manipulation portion body 310A, a first angle knob 320, a second angle knob 330, an air supply button 350, a suction button 351, and various buttons 352.

When the manipulation portion body 310A is compared with the manipulation portion body 310 of the controller 300 of the above-described embodiment, a position to which the manipulation cable 301 is connected is different. The manipulation portion body 310A includes a manipulation cable connection portion 313 to which the manipulation cable 301 is connected.

The manipulation cable connection portion 313 is provided near the various buttons 352 in the upward direction UPR of the manipulation portion body 310A. The manipulation cable connection portion 313 extends from the back surface 311 of the manipulation portion body 310A in the left direction LH. The manipulation cable connection portion 313 may extend from the side surface of the left direction LH of the manipulation portion body 310A in the left direction LH.

The manipulation cable connection portion 313 is provided at a position equivalent to a position where the universal cable is connected in the manipulation portion of a conventional flexible endoscope. Therefore, the physician S can stably hold the controller 300A by sandwiching the manipulation cable connection portion 313 between a thumb and an index finger of his or her left hand L like the manipulation portion of the conventional flexible endoscope.

The controller 300A may communicate with the drive device 200 through wireless communication and the manipulation cable 301 may not be connected to the controller 300A. With wireless communication, the left hand L can hold the controller 300A more freely. Even if communication is wireless, in order to make it easier to hold the controller 300A between the thumb and the index finger of the left hand L, the manipulation cable connection portion 313 to which the manipulation cable 301 is not connected may be provided in the manipulation portion body 310A. The physician S can stably hold the controller 300A by sandwiching the manipulation cable connection portion 313 between the thumb and the index finger of his or her left hand L.

In the above-described embodiment, the motorized endoscope system 1000 may further include a known endoscope mounting instrument such as a smart shooter (registered trademark). By using the endoscope mounting instrument, the physician S can perform a forward/rearward manipulation of the treatment tool 400 while holding the insertion portion 110 with his or her right hand R.

In the above-described embodiment, according to the motorized endoscope system 1000, the wire drive portion 250 can be controlled so that the difference between the first angle ϕ and the second angle $\phi_{ref}$ is eliminated when the first angle ϕ (the first bending amount), which is an angular displacement amount of the bending portion 112 calculated on the basis of the driving amount of the wire drive portion 250 is different from the second angle $\phi_{ref}$ (the second bending amount), which is an angular displacement amount of the bending portion 112 calculated on the basis of the movement amount (Δθ) of the first angle knob 320 or the second angle knob 330. However, a parameter used for controlling the wire drive portion 250 is not limited to the angle. For example, the motorized endoscope system 1000 can control the wire drive portion 250 so that the difference between the first bending amount and the second bending amount is eliminated when the driving amount of the wire drive portion 250 is designated as the first driving amount (the first bending amount) and the first driving amount (the first bending amount) is different from the second driving amount (the second bending amount) that is the driving amount of the wire drive portion 250 calculated on the basis of the movement amount (Δθ) of the first angle knob 320 or the second angle knob 330. Also, the motorized endoscope system 1000 can control the wire drive portion 250 so that the difference between the first wire displacement amount and the second wire displacement amount is eliminated when a displacement amount (a traction amount or a relaxation amount) of the bending wire 160 is designated as a first wire displacement amount (a first bending amount) and the first wire displacement amount (the first bending amount) is different from a second wire displacement amount (a second bending amount) that is a displacement amount of the bending wire 160 calculated on the basis of the movement amount (Δθ) of the first angle knob 320 or the second angle knob 330. The present invention is not limited to this, if a parameter can used to identify a change in a bending shape of the bending portion 112, it can be employed as the first bending amount or the second bending amount.

In the above-described embodiment, the motorized endoscope system 1000 may further include a function for adjusting the responsiveness of the bending portion 112 to a manipulation input to the first angle knob 320 or the second angle knob 330.

For example, there may be a delay between the time when the physician S rotates the first angle knob 320 or the second angle knob 330 and the time when the bending portion 112 begins to bend. In particular, a delay may occur when the bending angle ϕ of the bending portion 112 is inverted or when the bending portion 112 is close to a straight shape. Here, the reversal of the bending angle ϕ indicates that it is bent in the opposite direction from an immediately previous bending direction and a bending direction is switched. The above-described responsiveness indicates a degree of this delay. For example, when the bending portion 112 is close to the straight shape and the bending wire 160 is slack, there may be a delay between the time when the physician S rotates the first angle knob 320 or the second angle knob 330 and the time when the bending portion 112 begins to bend. Also, in a state in which the bending portion 112 is bent, when it returns to a straight shape after bending or when it is bent again before returning to the straight shape, the operation of the bending portion 112 is delayed due to hysteresis when the bending angle ϕ is inverted.

For example, the controller includes a switch for adjusting responsiveness (a responsiveness adjustment switch). The various buttons 352 provided in the controller 300 of the above-described embodiment may be used as the responsiveness adjustment switch. For example, when the physician S presses the various buttons 352 of the controller 300, the motorized endoscope system 1000 performs control for adjusting the responsiveness of the bending portion 112 for the manipulation input to the first angle knob 320 or the second angle knob 330.

The drive controller 260 changes a control parameter and changes responsiveness when the responsiveness adjustment switch is pressed. Examples of the control parameter for changing the responsiveness include the ratio of the traction amount of the bending wire 160 to the movement amount (the rotation amount) of the first angle knob 320 or the second angle knob 330.

By manipulating the responsiveness adjustment switch and adjusting the responsiveness, the physician S can manipulate the motorized endoscope system 1000 in a state in which any responsiveness is set and manipulability is improved. The responsiveness may be adjusted quick or slow on the basis of the manipulation input to the responsiveness adjustment switch.

For example, the controller device may include a lever or sliding knob as a responsiveness adjustment switch and the responsiveness may be adjusted quick or slow according to the manipulation direction of the knob. Also, the controller may include a plurality of responsiveness adjustment switches, a responsiveness adjustment switch for quick response, and a responsive adjustment switch for slow response.

Also, a responsiveness adjustment may be performed in combination with an adjustment automatically performed by the drive controller 260 and an adjustment performed by the drive controller 260 on the basis of a manipulation input by the physician S to the responsiveness adjustment switch. For example, in the responsiveness adjustment, a rough (coarse) adjustment may be performed automatically and a fine adjustment may be performed by the physician S manipulating the responsiveness adjustment switch.

For example, an offset may be set and controlled in accordance with the manipulation input by the physician S to the responsiveness adjustment switch with respect to a control parameter automatically estimated by the drive controller 260 to adjust the responsiveness.

When the controller includes the responsiveness adjustment switch, manipulability can be improved because the physician S can adjust the responsiveness of the bending portion 112 for the manipulation input to the first angle knob 320 or the second angle knob 330 to any degree (quickly, slowly, or the like).

Second Embodiment

A motorized endoscope system 1000B according to a second embodiment of the present invention will be described with reference to FIGS. 20 to 27. In the following description, components identical to the already described components are denoted by reference signs and description thereof will be omitted.

[Motorized Endoscope System 1000B]

As shown in FIG. 1, the motorized endoscope system 1000B includes an endoscope 100, a drive device 200B, a controller 300B, a treatment tool 400, a video control device 500, and a display device 900. The drive device 200B and the video control device 500 constitute a control device 600B that controls the motorized endoscope system 1000B.

[Controller 300B]

Figure 20:
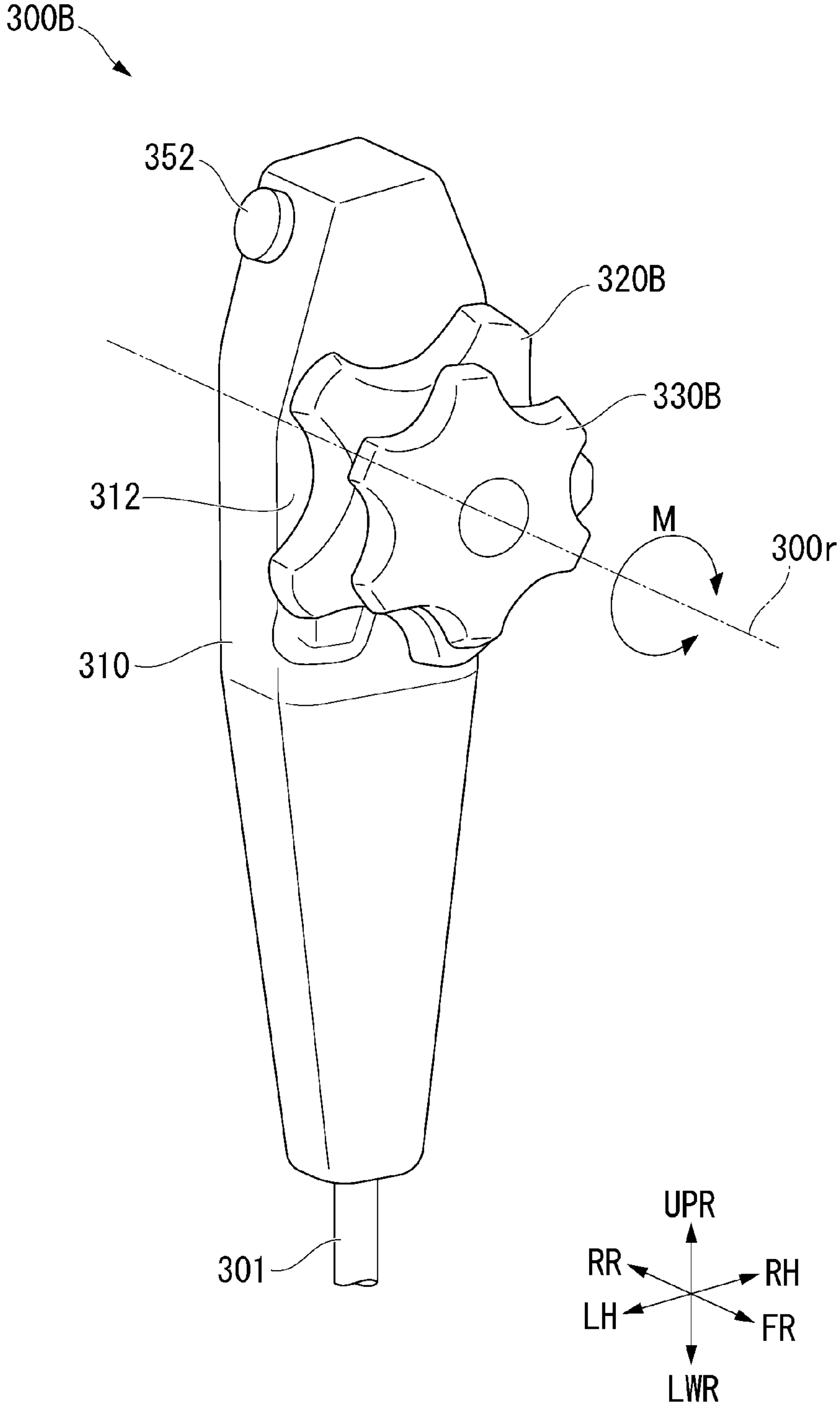
FIG. 20 is a perspective view of a controller of a medical manipulator system according to a second embodiment.

FIG. 20 is a perspective view of the controller 300B. The controller 300B includes a manipulation portion body 310, a first angle knob 320B, a second angle knob 330B, an air supply button 350, a suction button 351, and various buttons 352.

Like the first angle knob 320 and the second angle knob 330 of the first embodiment, the first angle knob 320B and the second angle knob 330B are rotationally attached to the front surface 312 with respect to the manipulation portion body 310 and are interfaces to which a bending manipulation of bending the bending portion 112 is input. The first angle knob 320B and the second angle knob 330B rotate in a rotation direction M around the same rotation axis 300*r*.

The first angle knob 320B and the second angle knob 330B have an encoder (not shown) that detects a rotation angle, the number of rotations, and the like in the rotation manipulation input to the first angle knob 320B and the second angle knob 330B. A detection result of the encoder is transmitted to the drive device 200B.

Figure 21:
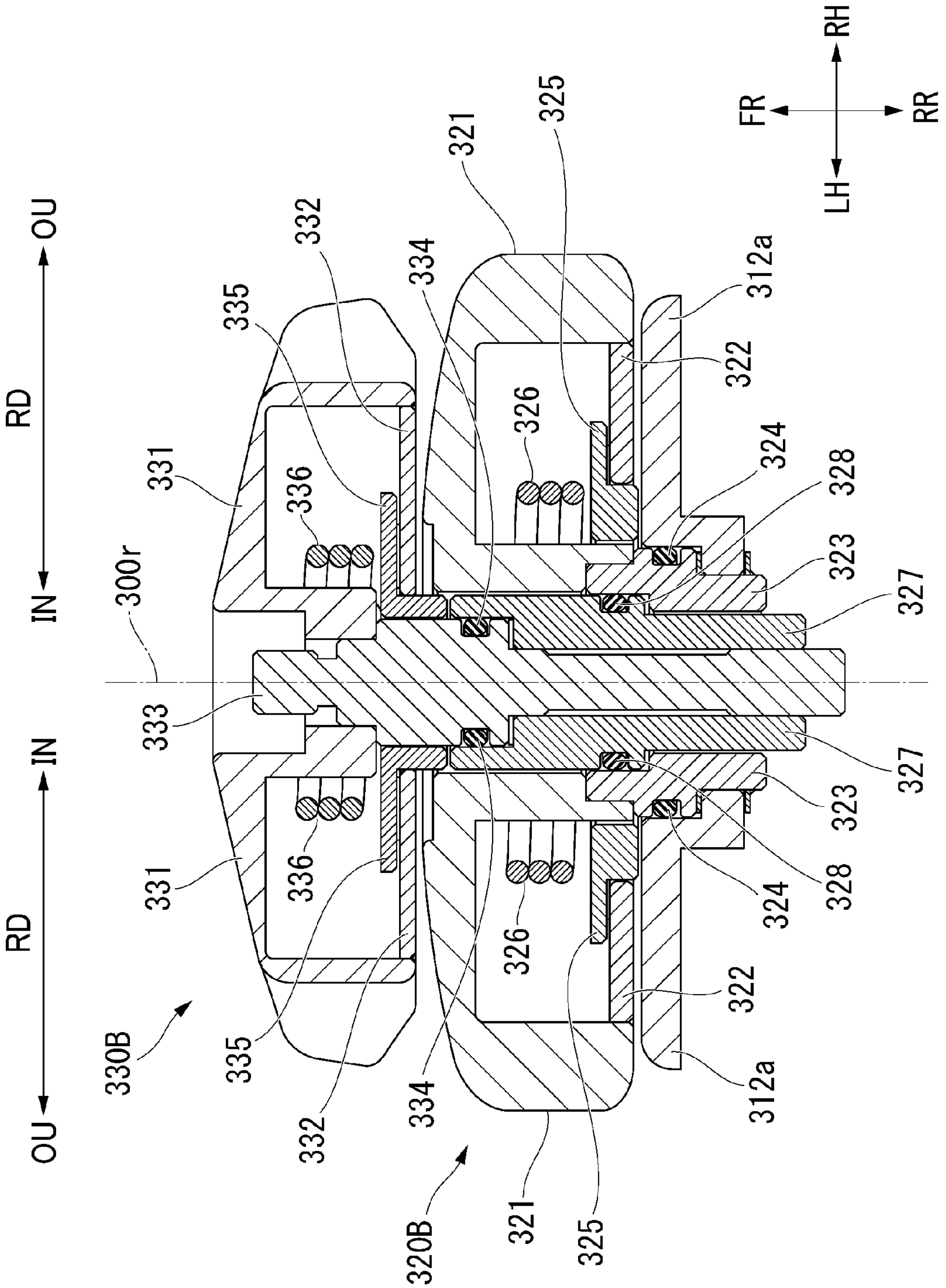
FIG. 21 is a cross-sectional view of a first angle knob and a second angle knob of the controller.
Figure 22:
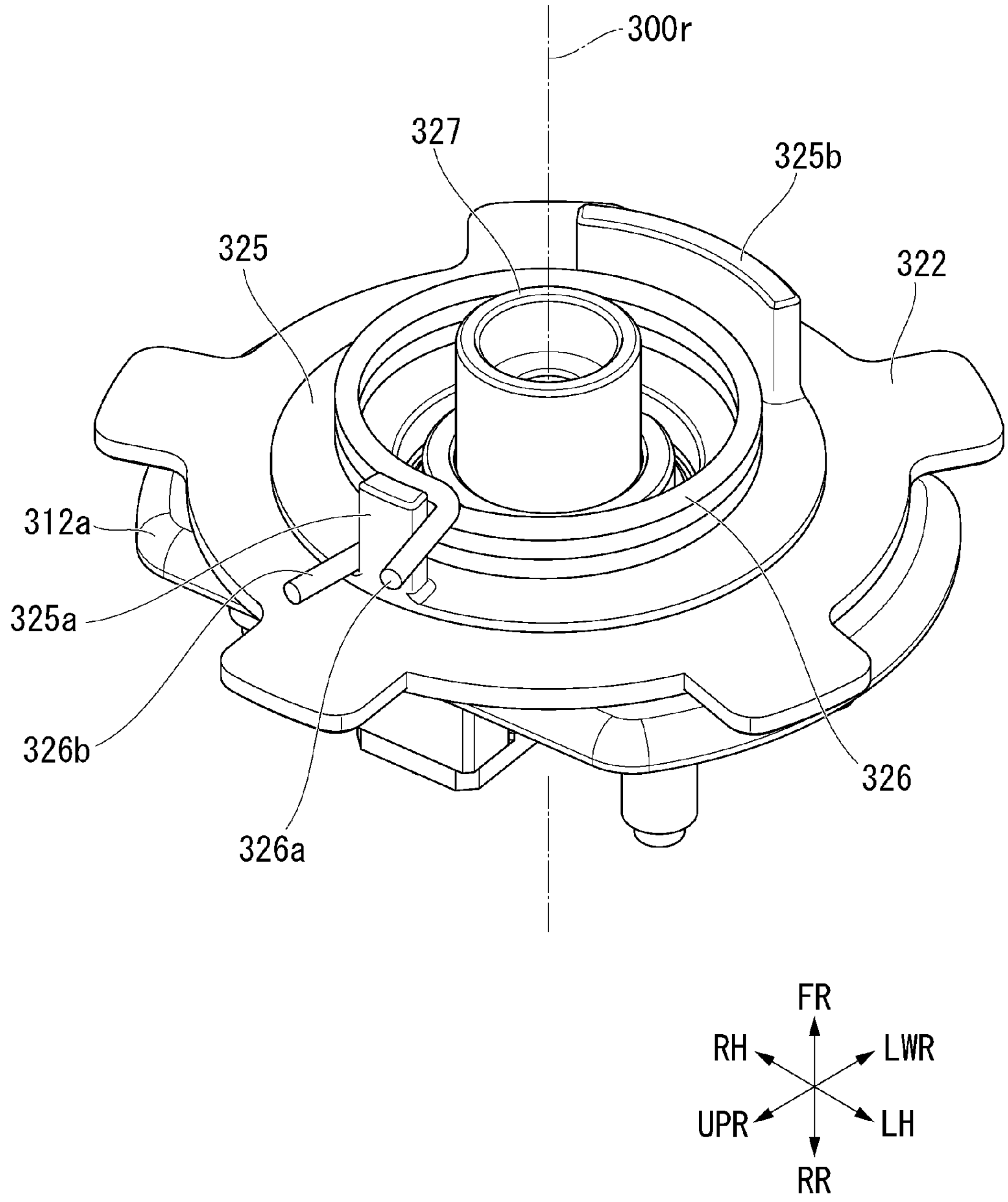
FIG. 22 is a perspective view showing a part of the first angle knob.
Figure 23:
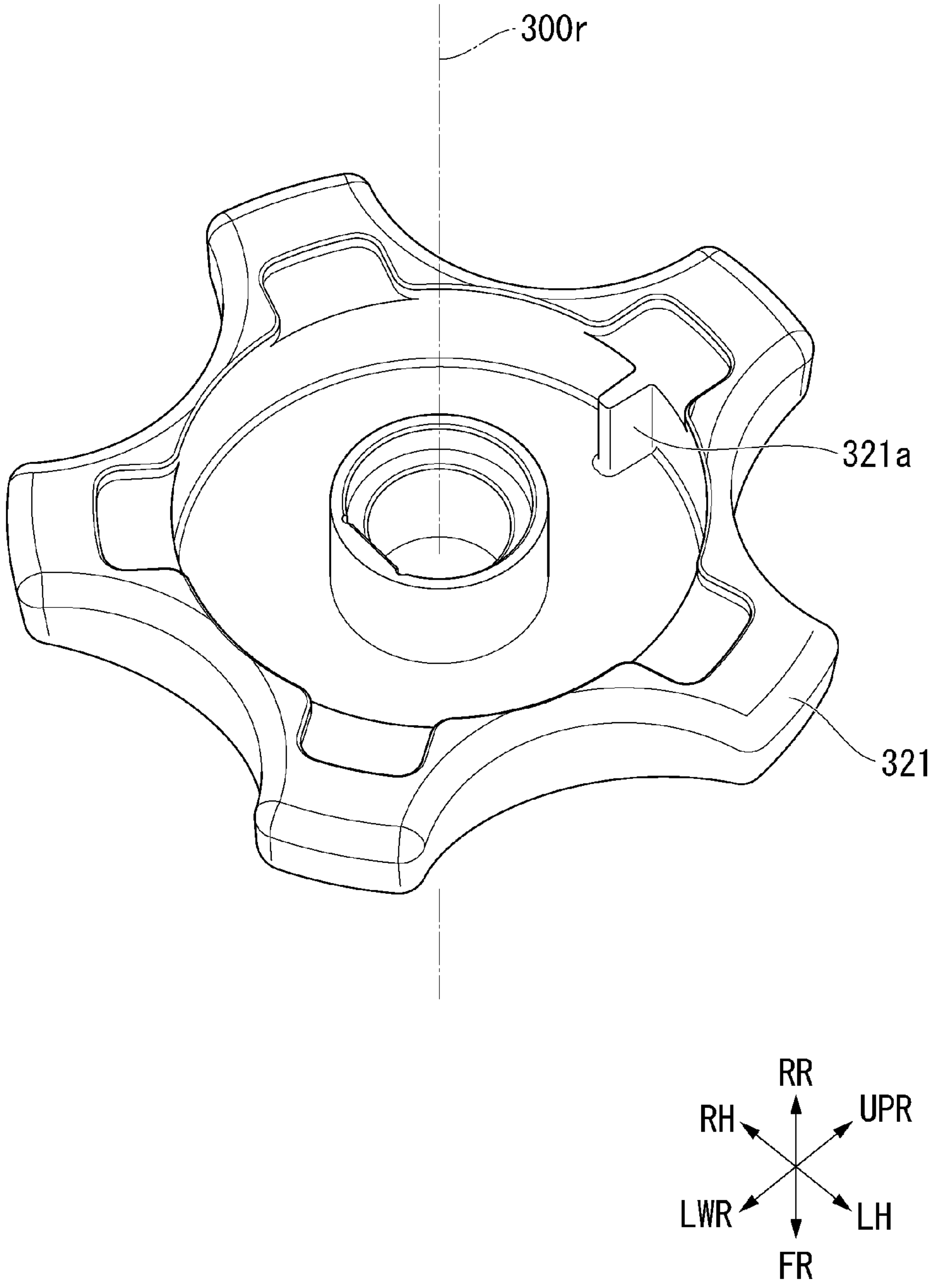
FIG. 23 is a perspective view showing a first upper cover of the first angle knob.

FIG. 21 is a cross-sectional view of the first angle knob 320B and the second angle knob 330B. FIG. 22 is a perspective view showing a part of the first angle knob 320B. FIG. 23 is a perspective view showing a back surface of the first upper cover 321 of the first angle knob 320B.

In the following description, as shown in FIG. 21, a direction perpendicular to the rotation axis 300*r* is defined as a "radial direction RD," a direction away from the rotation axis 300*r* is defined as an "outer side OU," and a direction approaching the rotation axis 300*r* is defined as an "inner side IN."

When the first angle knob 320B and the second angle knob 330B rotate in a direction away from the origin OP (a first direction M1) using the rotation axis 300*r* as the rotation center and have an elastic member (a first elastic member 326 and a second elastic member 336) biased in a direction returning to the origin OP (a second direction M2).

The first angle knob 320B and the second angle knob 330B are attached to the front surface 312 of the controller 300 via a knob fixing portion 312*a*. The first angle knob 320B and the second angle knob 330B may be directly attached to the front surface 312 without going through the knob fixing portion 312*a*, but the first angle knob 320B and the second angle knob 330B can be easily removed from the controller 300 when components are replaced or the like through the knob fixing portion 312*a*.

The first angle knob 320B includes a first upper cover 321, a first lower cover 322, a first knob shaft 323, a first O-ring 324, a first spring base 325, a first elastic member 326, a fixed shaft 327, and a third O-ring 328.

The first upper cover 321 has a substantially cylindrical shape with the rotation axis 300*r* as the central axis and forms the outer shape of the first angle knob 320B that the physician S touches when performing a manipulation with his or her left hand L. As shown in FIGS. 21 and 23, the first upper cover 321 has a substantially cylindrical concave shape that opens in a rearward direction RR. The first spring base 325 and the first elastic member 326 are stored in this concave shape.

The first lower cover 322 is a substantially disk shape centered on the rotation axis 300*r* and has a substantially circular opening centered on the rotation axis 300*r*. The first lower cover 322 is attached to the first upper cover 321 in the rearward direction RR and covers a part of the outer side OU in the radial direction RD in the opening of the rearward direction RR in the concave shape formed on the first upper cover 321.

The first knob shaft 323 is a rotation shaft portion for the first angle knob 320B to rotate using the rotation axis 300*r* as the rotation center. The first knob shaft 323 has a substantially cylindrical shape with the rotation axis 300*r* as the central axis and is connected to the knob fixing portion 312*a* via the first O-ring 324 attached to an outer circumferential surface. The first O-ring 324 and the knob fixing portion 312*a* are in contact in the radial direction RD. The first knob shaft 323 causes the first O-ring 324 to slide with respect to the knob fixing portion 312*a* and can rotate with respect to the knob fixing portion 312*a* with the rotation axis 300*r* as the rotation center.

Because the end portion of the first upper cover 321 in the rearward direction RR and the end portion of the first knob shaft 323 in the forward direction FR are connected, the first upper cover 321 and the first lower cover 322 can rotate in the rotation direction M with respect to the knob fixing portion 312*a* with the rotation axis 300*r* as the rotation center together with the first knob shaft 323.

The first spring base 325 has a substantially cylindrical shape with the rotation axis 300*r* as the central axis and covers a part of the inner side IN in the radial direction RD at the opening of the rearward direction RR in the concave shape formed on the first upper cover 321. The first spring base 325 is connected to the knob fixing portion 312*a*. Because the rotation operation is regulated in the rotation direction M by a regulation pin (not shown) protruding from the knob fixing portion 312*a* in the forward direction FR, the first spring base 325 does not rotate in the rotation direction M with respect to the knob fixing portion 312*a*.

As shown in FIG. 22, the first spring base 325 has a first regulation portion 325*a* and a second regulation portion 325*b* protruding from the forward direction FR. The first regulation portion 325*a* is provided at the end portion of the first spring base 325 in the upward direction UPR. The second regulation portion 325*b* is provided at the end portion of the first spring base 325 in the downward direction LWR.

As shown in FIG. 22, the first elastic member 326 is a spring member (a torsion coil spring) provided on the first spring base 325 in the forward direction FR. The first elastic member 326 has a first arm portion 326*a* and a second arm portion 326*b* extended in the upward direction UPR at both ends of a coil portion wound around the rotation axis 300*r*. The first arm portion 326*a* and the second arm portion 326*b* are arranged to sandwich the first regulation portion 325*a* of the first spring base 325 in the rotation direction M of the first angle knob 320B. Therefore, the rotation operation of the first elastic member 326 in the rotation direction M is regulated by the first regulation portion 325*a* and does not rotate with respect to the first spring base 325.

When a bending manipulation is input to the first angle knob 320B, the first upper cover 321, the first lower cover 322, the first knob shaft 323, and the first O-ring 324 rotate in the rotation direction M with respect to the knob fixing portion 312*a* with the rotation axis 300*r* as the rotation center. On the other hand, the first spring base 325 and the first elastic member 326 do not rotate.

Figure 24:
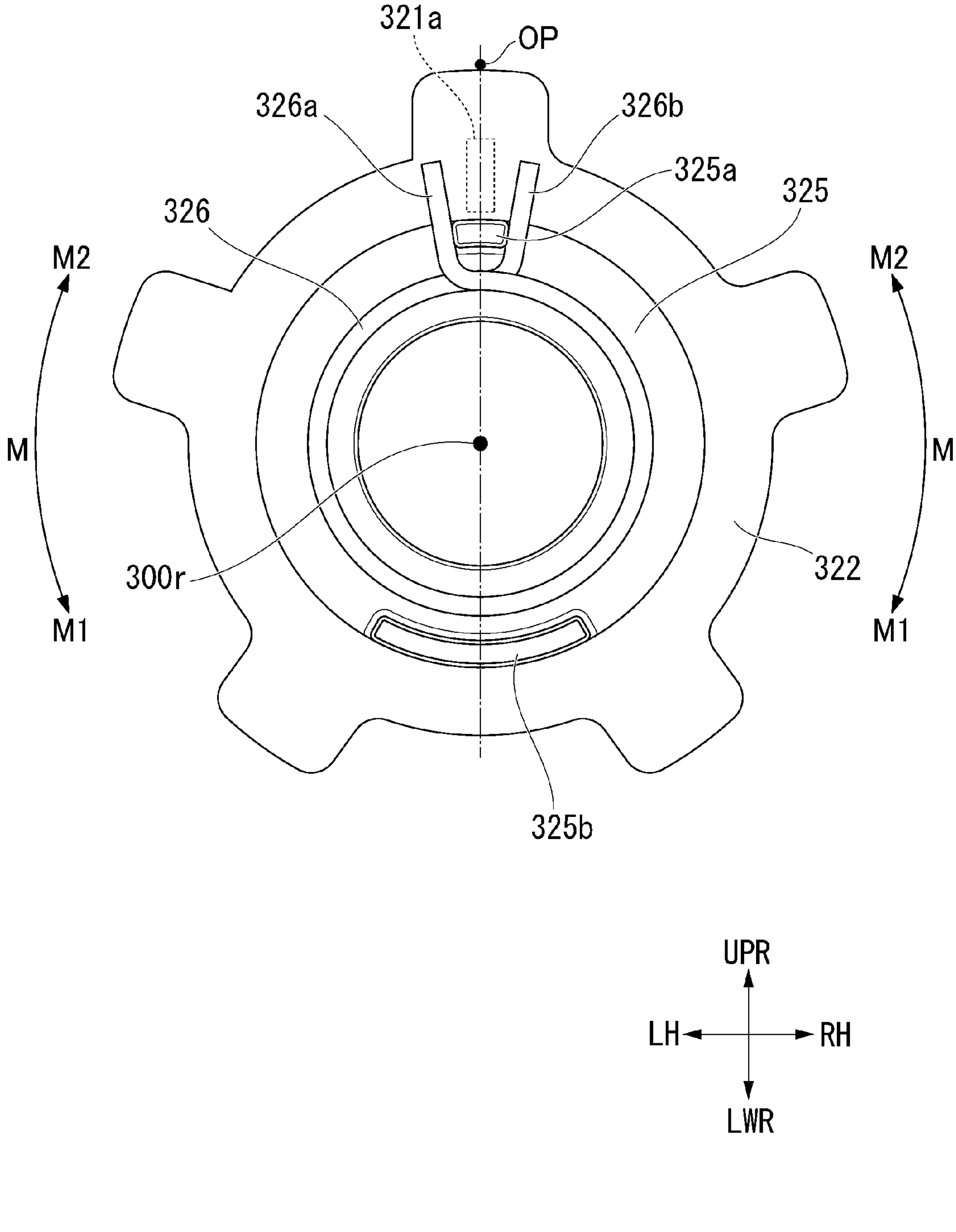
FIG. 24 is a front view showing a part of the first angle knob.

Here, as shown in FIG. 23, a first contact portion 321*a* extending in the radial direction RD is provided in the concave shape of the first upper cover 321 in the upward direction UPR. Also, as shown in FIG. 24, in the first angle knob 320B, the first contact portion 321*a* of the first upper cover 321 is arranged on the first regulation portion 325*a* in the first spring base 325 in the upward direction UPR. Therefore, the first contact portion 321*a* of the first upper cover 321 is arranged to be sandwiched between the first arm portion 326*a* and the second arm portion 326*b* of the first elastic member 326 in the rotation direction M.

In the present embodiment, the first angle knob 320B when the first contact portion 321*a* is located at the position shown in FIG. 24 (directly above the rotation axis 300*r* in the upward direction UPR) is located at an initial position where the origin OP and the reference point L1 at the first angle knob 320B are aligned.

When the first angle knob 320B rotates in the direction away from the origin OP (the first direction M1), the first contact portion 321*a* comes into contact with the first arm portion 326*a* or the second arm portion 326*b* of the first elastic member 326 in the rotation direction M. When the first arm portion 326*a* or the second arm portion 326*b* is pushed by the first contact portion 321*a* in the first direction M1, the coil portion of the first elastic member 326 is deformed and the first arm portion 326*a* or the second arm portion 326*b* moves together with the first contact portion 321*a* in the first direction M1.

At this time, the first contact portion 321*a* is biased in the direction returning to the origin OP (the second direction M2) according to the elasticity possessed by the coil portion of the first elastic member 326. Therefore, when the physician S rotates the first angle knob 320B in the first direction M1 with his or her left hand L and releases his or her left hand L from the first angle knob 320B, the first angle knob 320B is biased by the first elastic member 326 and rotates in the second direction M2.

Although the force (elastic force) with which the first elastic member 326 biases the first angle knob 320B in the second direction M2 can be adjusted as appropriate by changing the material and shape of the first elastic member 326, a force required to rotate the first angle knob 320B in the first direction M1 also becomes large if the biasing force is strong. Therefore, it is desirable that the force with which the first elastic member 326 biases the first angle knob 320B in the second direction M2 be a force that is not strong to return the reference point L1 of the first angle knob 320B to the origin OP and has a degree to which the biased first angle knob 320B is stopped near the origin OP.

When the first angle knob 320B rotates about 180° from the origin OP, the first angle knob 320B does not rotate anymore because the first arm portion 326*a* or the second arm portion 326*b* comes into contact with the second regulation portion 325*b* in the rotation direction M. Therefore, a deformation amount of the first elastic member 326 can be suppressed and the first elastic member 326 can be prevented from being damaged.

The fixed shaft 327 has a substantially cylindrical shape with the rotation axis 300*r* as the central axis. The fixed shaft 327 is arranged on the inner side IN of the first upper cover 321 and the first knob shaft 323 as shown in FIG. 21. The end portion of the fixed shaft 327 in the rearward direction RR is connected to the knob fixing portion 312*a* (not shown). Because the fixed shaft 327 is fixed to the knob fixing portion 312*a* by a screw or the like, it does not rotate in the rotation direction M with respect to the knob fixing portion 312*a*.

The third O-ring 328 is attached to the outer circumferential surface of the fixed shaft 327 and is in contact with the first knob shaft 323 in the radial direction RD. When the first angle knob 320B rotates, the inner circumferential surface of the first knob shaft 323 and the third O-ring 328 slide and the first knob shaft 323 rotates.

The second angle knob 330B includes a second upper cover 331, a second lower cover 332, a second knob shaft 333, a second O-ring 334, a second spring base 335, and a second elastic member 336. The second angle knob 330B basically includes components having functions similar to those of the components of the first angle knob 320B.

The second upper cover 331 has a substantially cylindrical shape with the rotation axis 300*r* as the central axis and forms the outer shape of the second angle knob 330B that the physician S touches when performing a manipulation with his or her left hand L. As shown in FIG. 21, the second upper cover 331 has a substantially cylindrical concave shape opened in the rearward direction RR. The second spring base 335 and the second elastic member 336 are stored in this concave shape.

The second lower cover 332 has a substantially disk shape centered on the rotation axis 300*r* and has a substantially circular opening centered on the rotation axis 300*r*. The second lower cover 332 is attached to the second upper cover 331 in the rearward direction RR and covers a part of the outer side OU in the radial direction RD at the opening in the concave shape formed in the second upper cover 331 in the rearward direction RR.

The second knob shaft 333 is a rotating shaft portion for the second angle knob 330B to rotate using the rotation axis 300*r* as the rotation center. The second knob shaft 333 has a substantially cylindrical shape with the rotation axis 300*r* as the central axis and is arranged on the inner side IN of the fixed shaft 327. The second knob shaft 333 is connected to the fixed shaft 327 via the second O-ring 334 attached to the outer circumferential surface. The second O-ring 334 and the fixed shaft 327 are in contact in the radial direction RD. The second knob shaft 333 causes the second O-ring 334 to slide with respect to the fixed shaft 327 and can rotate with respect to the fixed shaft 327 with the rotation axis 300*r* as the rotation center.

The second upper cover 331 is connected to the second knob shaft 333 and can be rotated together with the second knob shaft 333 with the rotation axis 300*r* as the rotation center. Therefore, the first upper cover 321 and the first lower cover 322 can rotate in the rotation direction M with respect to the fixed shaft 327 with the rotation axis 300*r* as the rotation center together with the first knob shaft 323.

The second spring base 335 has a substantially cylindrical shape with the rotation axis 300*r* as the central axis and covers a part of the inner side IN in the radial direction RD at the opening in the concave shape formed in the second upper cover 331 in the rearward direction RR. The second spring base 335 is connected to the fixed shaft 327 and does not rotate in the rotation direction M with respect to the fixed shaft 327.

Like the first spring base 325, the second spring base 335 has a third regulation portion (not shown) and a fourth regulation portion (not shown) protruding in the forward direction FR. The third regulation portion is provided at the end portion of the second spring base 335 in the upward direction UPR. The fourth regulation portion is provided at the end portion of the second spring base 335 in the downward direction LWR.

The second elastic member 336 is a spring member (a torsion coil spring) provided on the second spring base 335 in the forward direction FR. Like the first elastic member 326, the second elastic member 336 has a third arm portion (not shown) and a fourth arm portion (not shown) extended in the upward direction UPR at both ends of the coil portion wound around the rotation axis 300*r*. The third arm portion and the fourth arm portion are arranged by sandwiching the third regulation portion of the second spring base 335 in the rotation direction M of the second angle knob 330B. Therefore, the rotation operation of the second elastic member 336 is regulated by the third regulation portion in the rotation direction M and does not rotate with respect to the second spring base 335.

When a bending manipulation is input to the second angle knob 330B, the second upper cover 331, the second lower cover 332, the second knob shaft 333, and the second O-ring 334 rotate in the rotation direction M with respect to the fixed shaft 327 with the rotation axis 300*r* as the rotation center. On the other hand, the second spring base 335 and the second elastic member 336 do not rotate.

Like the first upper cover 321, a second contact portion (not shown) extending in the radial direction RD is provided in the concave shape of the second upper cover 331 in the upward direction UPR. Also, in the second angle knob 330B, the second contact portion of the second upper cover 331 is arranged on the third regulation portion in the second spring base 335 in the upward direction UPR. Therefore, the second contact portion of the second upper cover 331 is arranged to be sandwiched between the third arm portion and the fourth arm portion of the second elastic member 336 in the rotation direction M.

In the present embodiment, when the second contact portion of the second upper cover 331 is located directly above the rotation axis 300*r* in the upward direction UPR like the first angle knob 320B, the second angle knob 330B is located at an initial position where the origin OP and the reference point (not shown) at the second angle knob 330B are aligned.

When the second angle knob 330B rotates in a direction away from the origin OP (the first direction M1) like the first angle knob 320B, the second contact portion comes into contact with the third arm portion or the fourth arm portion of the second elastic member 336 in the rotation direction M. When the third arm portion or fourth arm portion is pushed by the second contact portion in the first direction M1, the coil portion of the second elastic member 336 is deformed and the third arm portion or fourth arm portion moves in the first direction M1 together with the second contact portion.

At this time, the second contact portion is pushed in a direction returning to the origin OP (the second direction M2) by the elasticity possessed by the coil portion of the second elastic member 336. Therefore, when the physician S rotates the second angle knob 330B in the first direction M1 with his or her left hand L and releases his or her left hand L from the second angle knob 330B, the second angle knob 330B is biased by the second elastic member 336 and rotates in the second direction M2.

Although the force (elastic force) with which the second elastic member 336 biases the second angle knob 330B in the second direction M2 can be adjusted as appropriate by changing the material and shape of the second elastic member 336, the force required to rotate the second angle knob 330B in the first direction M1 also becomes large if the biasing force is strong. Therefore, it is desirable that the force with which the second elastic member 336 biases the second angle knob 330B in the second direction M2 be a force that is not strong to cause the second angle knob 330B to return to the origin OP and has a degree to which the biased second angle knob 330B is stopped near the origin OP.

When the second angle knob 330B rotates about 180° from the origin OP like the first angle knob 320B, the second angle knob 330B does not rotate anymore because the third arm portion or the fourth arm portion comes into contact with the fourth regulation portion in the rotation direction M. Therefore, a deformation amount of the second elastic member 336 can be suppressed and the second elastic member 336 can be prevented from being damaged.

The second knob shaft 333 of the second angle knob 330B is arranged on the inner side IN of the fixed shaft 327 of the first angle knob 320B as shown in FIG. 21. Therefore, the rotation operations of the first angle knob 320B and the second angle knob 330B do not communicate with each other and only the angle knob rotated by the physician S rotates and the angle knob not manipulated by the physician S does not rotate when the physician S rotates the first angle knob 320B or the second angle knob 330B. As a result, it is possible to prevent the physician S from inputting an unintended bending manipulation to the controller 300B.

In the conventional flexible endoscope, when the physician releases his or her hand from the angle knob of the manipulation portion and no bending manipulation is input to the angle knob, a restoring force for returning the bent bending portion to a linear state is applied by a rubber or the like that forms an outer sheath. Also, the angle knob rotates in a direction returning to the origin in accordance with an operation of the bending portion that tries to return to the linear state by the restoring force.

When the first angle knob 320B and the second angle knob 330B have elastic members (the first elastic member 326 and the second elastic member 336), the physician S releases his or her hand from the first angle knob 320B and the second angle knob 330B and the first angle knob 320B and the second angle knob 330B are biased by the elastic members and rotate in a direction returning to the origin OP (the second direction M2). As a result, the motorized endoscope system 1000B can provide the physician S with manipulability close to that of the conventional flexible endoscope.

[Drive Device 200B]

Figure 25:
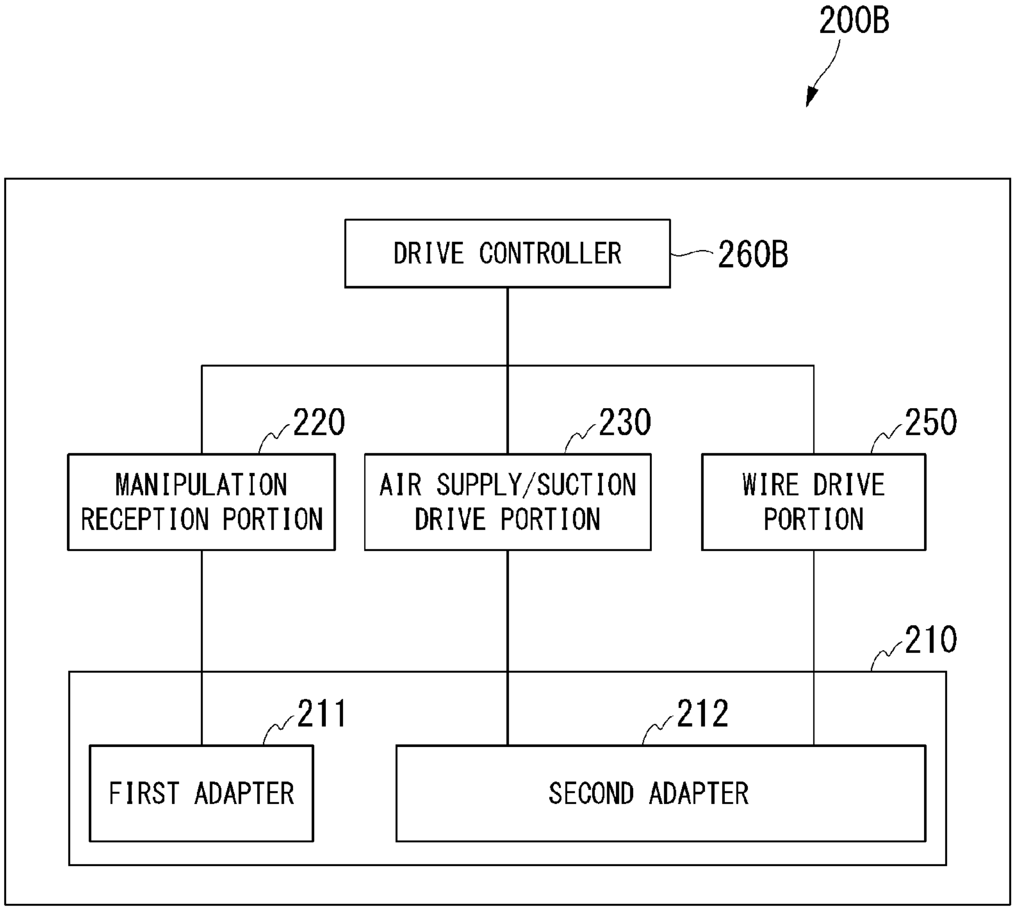
FIG. 25 is a functional block diagram of a drive device in the medical manipulator system.

FIG. 25 is a functional block diagram of the drive device 200B.

The drive device 200B includes an adapter 210, a manipulation reception portion 220, an air supply/suction drive portion 230, a wire drive portion 250, and a drive controller 260B.

The drive controller 260B has a configuration similar to that of the drive controller 260 of the first embodiment and a method of controlling the wire drive portion 250 is different from that of the drive controller 260.

[Operation of Motorized Endoscope System 1000B]

Next, an operation of the motorized endoscope system 1000B of the present embodiment will be described. Specifically, a procedure for observing and treating an affected area formed in the canal wall in the large intestine using the motorized endoscope system 1000B will be described.

Figure 26:
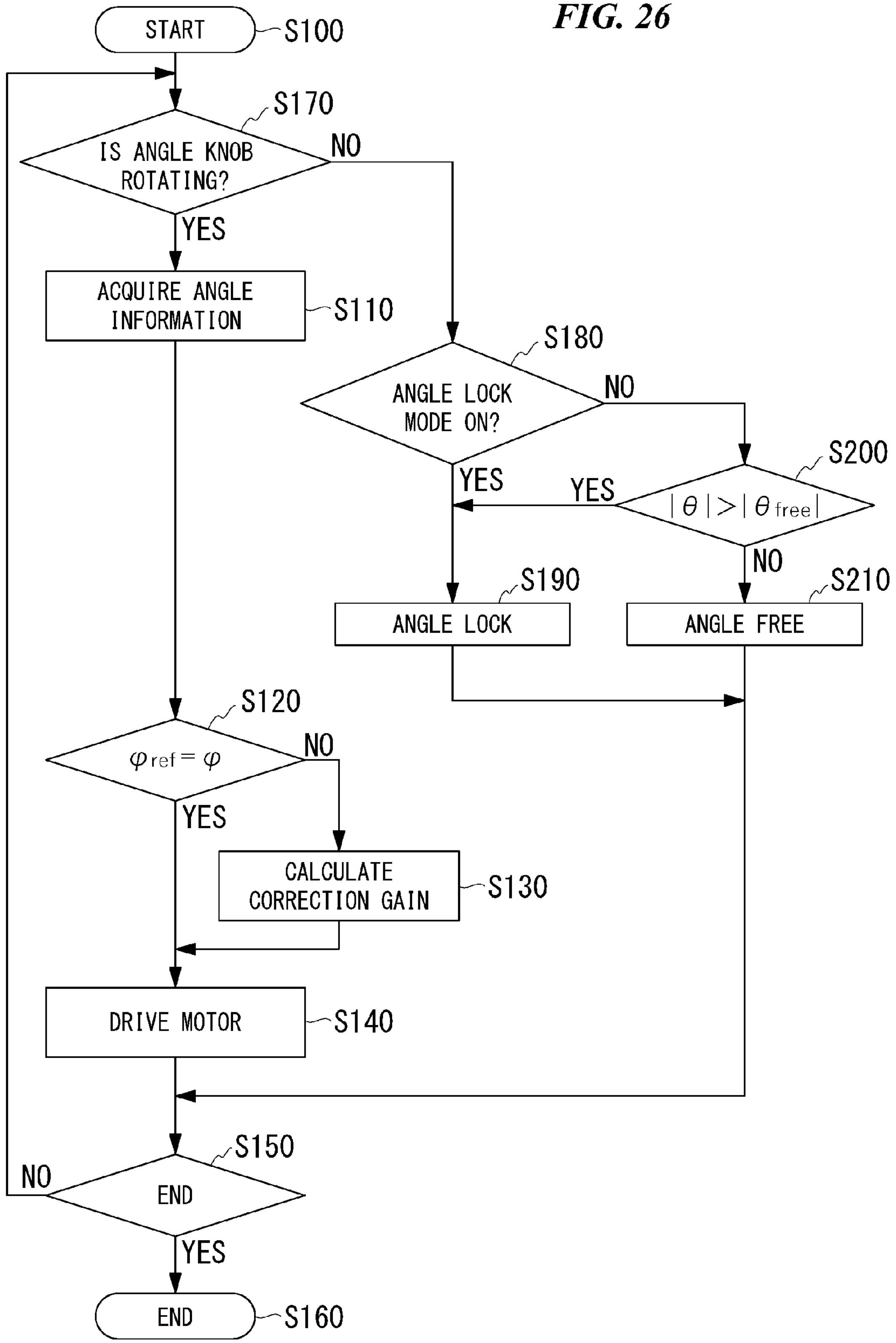
FIG. 26 is a flowchart showing control of the medical manipulator system in the drive device.

FIG. 26 is a control flowchart of the drive controller 260B in the motorized endoscope system 1000B. The control flowchart of the drive controller 260B further includes steps S170 to S210 with respect to the control flowchart of the drive controller 260 of the first embodiment shown in FIG. 17.

In the following description, the description will be given with reference to the control flowchart of the drive controller 260B of the control device 600B shown in FIG. 26. When the control device 600B is activated, the drive controller 260B performs initialization (step S100). Subsequently, the drive controller 260B (mainly the processor 261) executes step S170.

<Step S170>

In the following description, a control process of the drive controller 260B when a bending manipulation is input to the first angle knob 320B will be described. The drive controller 260B also performs a similar control process for the bending manipulation input to the second angle knob 330B.

The drive controller 260B acquires a detection result of the encoder provided by the controller 300B in step S170. At this time, it is acquired whether the first angle knob 320B is in a stationary or rotating state from information such as a rotation angle and a rotation direction of the first angle knob 320B acquired from the encoder.

When a bending manipulation is input to the first angle knob 320B and rotated in the first direction M1 or the second direction M2, the first angle knob 320B is in the rotating state. Also, when the first angle knob 320B rotated in the first direction M1 is biased to the first elastic member 326 and is rotating in the second direction M2, the first angle knob 320B is in the rotating state.

When a bending manipulation is not input to the first angle knob 320B and the reference point L1 in the first angle knob 320B is stopped near the origin OP, the first angle knob 320B is in a stopped state. Also, after the bending manipulation is input to the first angle knob 320B, when the first angle knob 320B is stopped at a certain angle by the left hand L or the like of the physician S, the first angle knob 320B is in the stopped state.

The drive controller 260B moves to step S110 when the first angle knob 320B is in the rotating state in step S170. Because the control step after step S110 is similar to a control step described using FIG. 17 in the first embodiment, description thereof will be omitted.

The drive controller 260B moves to step S180 when the first angle knob 320B is in the stopped state in step S170.

<Step S180>

The drive controller 260B acquires a setting state of an angle lock mode in step S180. Here, the angle lock mode indicates a control mode (angle lock control) in which the wire drive portion 250 is controlled on the basis of the position (angle) of the first angle knob 320B or the second angle knob 330B. On the other hand, there is angle-free control as a control mode other than the angle lock control. During angle-free control, the bending portion 112 passively bends with respect to an external force applied to the bending portion 112.

In the present embodiment, the drive controller 260B switches control between the angle lock control and the angle-free control by pushing the various buttons 352. By doing so, the physician S can easily switch the control between the angle lock control and the angle-free control when observing or treating the affected area. Also, a switching instruction between the angle lock control and the angle-free control may be input by the input device connected to the drive device 200B or the video control device 500 or the like.

When the drive controller 260B is set in the angle lock mode, the process moves to step S190.

<Step S190>

The drive controller 260B controls the wire drive portion 250 on the basis of the rotation angle of the first angle knob 320B in step S190. At this time, because the first angle knob 320B is stopped, the drive controller 260B controls the wire drive portion 250 so that the bending angle is maintained in the bending portion 112 based on the rotation angle of the first angle knob 320B.

The drive controller 260B executes step S150 after executing step S190. When control of the wire drive portion 250 continues in step S150, the drive controller 260B returns to step S170 and continues control of the wire drive portion 250. When the observation or treatment by the motorized endoscope system 1000B is completed, the drive controller 260B moves to step S160 and ends the process shown in FIG. 26.

<Step S200>

The drive controller 260B executes step S200 when the angle lock mode is not set in step S180.

Figure 27:
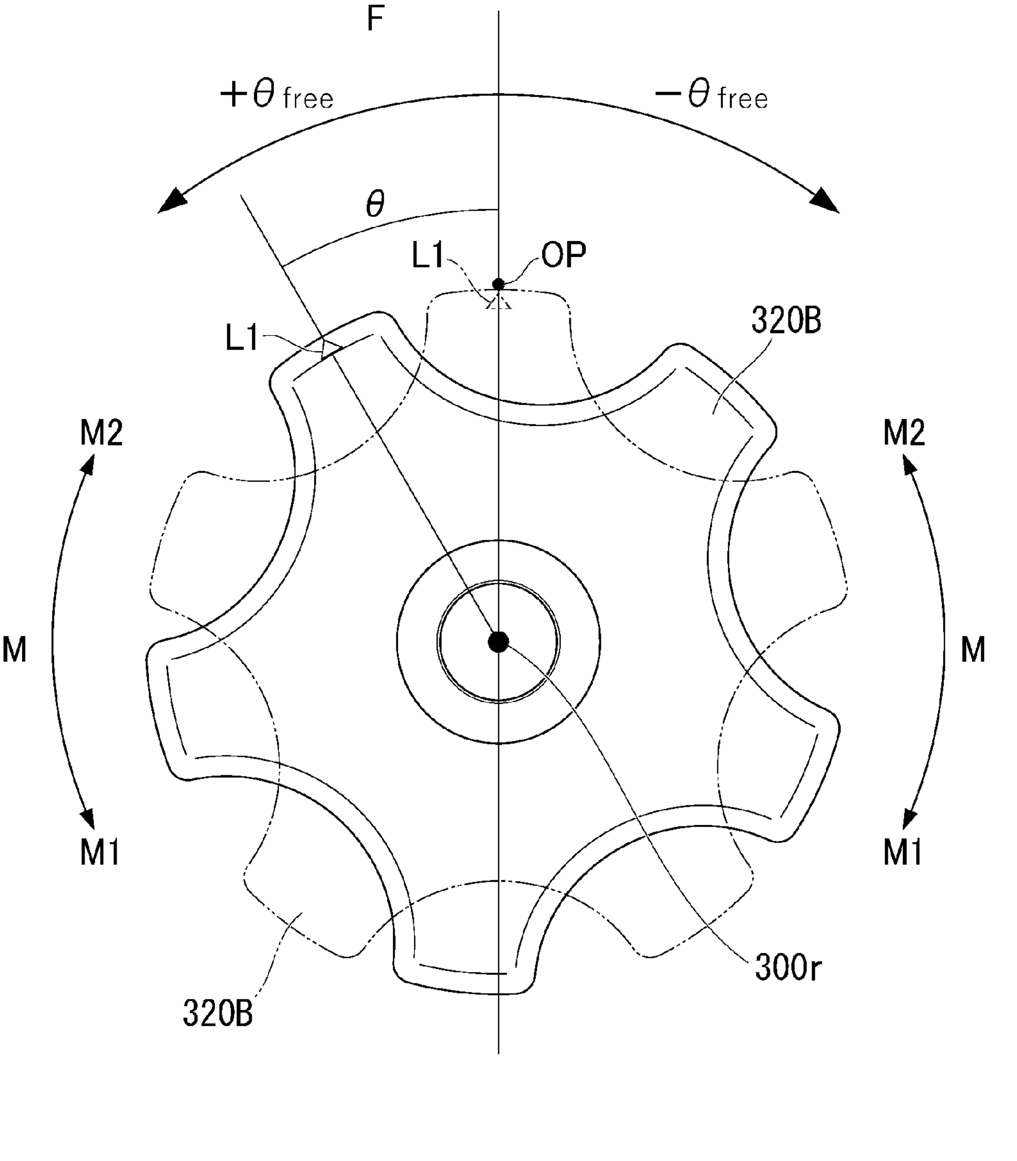
FIG. 27 is a front view showing a rotation operation of the first angle knob.

FIG. 27 is a front view showing a rotation operation in the rotation direction M of the first angle knob 320B.

In step S200, the drive controller 260B compares an absolute value of a rotation angle θ of the first angle knob 320B shown in FIG. 27 with an absolute value of an angle $\theta_{free}$. The rotation angle θ is a rotation angle from the origin OP in the first angle knob 320B.

Here, a range of $\pm\theta_{free}$ is referred to as a passive control range F. The passive control range F is a range (angle) in the vicinity of the origin OP in the first angle knob 320B or the second angle knob 330B. Also, the first angle knob 320B and the second angle knob 330B, which have rotated outside of the range of the passive control range F, are biased by the first elastic member 326 and the second elastic member 336 and return to the range that is the passive control range F.

When the absolute value of the rotation angle θ is larger than the absolute value of the angle $\theta_{free}$, the rotation angle θ is outside of the range that is the passive control range F. At this time, the drive controller 260B executes step S190 and executes angle lock control.

When the absolute value of the rotation angle θ is smaller than the absolute value of the angle $\theta_{free}$, the rotation angle θ is within the range that is the passive control range F. At this time, the drive controller 260B executes step S210.

<Step S210>

The drive controller 260B executes angle-free control in step S210. When the drive controller 260B is executing the angle-free control, the bending portion 112 is passively bent by an external force applied to the bending portion 112.

As the control method for the angle-free control, for example, there is tension control for performing control so that a tension difference between a pair of bending wires 160 (the upper bending wire 161*u* and the lower bending wire 161*d* or the left bending wire 161*l* and the right bending wire 161*r*) is eliminated. Also, a mechanism for preventing the driving force of the wire drive portion 250 from being transmitted to the bending wire 160 is provided and angle-free control may be implemented by switching a state between a state in which the driving force is transmitted and a state in which the driving force is not transmitted.

In the conventional flexible endoscope, the angle knob of the manipulation portion returns to the vicinity of the origin in accordance with the operation of the bending portion that tries to return to the linear state using the restoring force of the rubber or the like that forms the outer sheath when the physician releases his or her hand from the angle knob and no bending manipulation is input to the angle knob. Furthermore, when an external force is applied to the bending portion while the physician is releasing his or her hand from the angle knob, the bending portion is passively bent with respect to the applied external force.

By switching the control to the angle-free control when the rotation angle θ of the angle knob (the first angle knob 320B and the second angle knob 330B) is stopped within the range that is the passive control range F, the physician S releases his or her hand from the angle knob and the bending portion 112 is passively bent with respect to an external force applied to the bending portion 112 when the angle knob biased by the elastic member (the first elastic member 326 and the second elastic member 336) returns to the vicinity of the origin OP and is stopped. Therefore, the motorized endoscope system 1000B can provide manipulability close to that of the conventional flexible endoscope to the physician S.

In the passive control range F, any angle can be appropriately set and may be ±90° or ±60° and it is desirable that any angle be about ±45° from the viewpoint of manipulability. Also, the passive control range F in the first angle knob 320B and the passive control range F in the second angle knob 330B may be different angles.

The drive controller 260B executes step S150 after executing step S210. When continuing control of the wire drive portion 250 in step S150, the drive controller 260B returns to step S170 and continues control of the wire drive portion 250. When the observation or treatment by the motorized endoscope system 1000B is completed, the drive controller 260B moves to step S160 and ends the process shown in FIG. 26.

According to the motorized endoscope system 1000B according to the present embodiment, the first angle knob

320B and the second angle knob 330B are biased in a direction returning to the origin OP (the second direction M2) by the first elastic member 326 and the second elastic member 336 and return to the inside of the range that is the passive control range F when they rotate outside of the passive control range F. Also, when the first angle knob 320B and the second angle knob 330B are in a rotating state or is stopped outside of the range that is the passive control range F, the wire drive portion 250 is controlled on the basis of the rotation angle θ and the bending portion 112 passively bends with respect to the external force applied to the bending portion 112 when they are stopped within the range that is the passive control range F. As a result, the motorized endoscope system 1000B with improved manipulability can be provided.

Although the second embodiment of the present invention has been described above in detail with reference to the drawings, the specific configuration is not limited to the second embodiment and design changes and the like are also included without departing from the scope and spirit of the present invention. Also, the components shown in the above-described embodiments and modified examples can be appropriately combined and configured.

Although the first elastic member 326 and the second elastic member 336 that bias the first angle knob 320B and the second angle knob 330B are torsion coil springs in the above-described embodiment, the aspects of the first elastic member and the second elastic member are not limited thereto. Each of the first elastic member and the second elastic member may be an elastic member such as a rubber material.

Also, a damper such as a rotary damper may be used to adjust a force with which the first elastic member and the second elastic member bias the first angle knob and the second angle knob.

Also, a flat spiral spring may be employed for the first elastic member and the second elastic member. By using the flat spiral spring for the first elastic member and the second elastic member, the torque required to rotate the first angle knob 320B and the second angle knob 330B in the first direction M1 can be lightened, and, further, the torque required for rotation can be substantially uniform. Also, after the first angle knob 320B and the second angle knob 330B are rotated in the first direction M1, manipulability can be improved because the first angle knob 320B and the second angle knob 330B return to the second direction M2 when the physician S loosens the force of the finger (for example, the thumb).

Although the rotation angles θ of the first angle knob 320B and the second angle knob 330B are detected by an encoder provided in the controller 300B in the above-described embodiment, the form of the controller is not limited thereto. The controller may detect the rotation angles of the first angle knob and the second angle knob using a sensor other than an encoder such as a potentiometer.

Also, when the rotation angles of the angle knobs (the first angle knob and the second angle knob) are detected by a sensor that detects a relative angle rather than an absolute angle (for example, an incremental encoder), the angle knob can be adjusted to the origin (initial position) when the use of the motorized endoscope system starts and the tension of the bending wire can be initialized to detect the accurate rotation angle.

In this case, alignment can be easily performed by providing a marker (for example, the reference point L1 or the like) between the angle knob and the manipulation portion body. Also, alignment may be performed by providing the angle knob and the manipulation portion body with a protrusion shape that regulates the rotation operation of the angle knob located at the origin to some extent or alignment may be performed with an optical sensor or the like that can detect the position of the angle knob without contact.

Although the controller 300B is provided separately from the endoscope 100 in the above-described embodiment, the form of the controller is not limited thereto. The controller may be connected to the connection portion of the endoscope.

Figure 28:
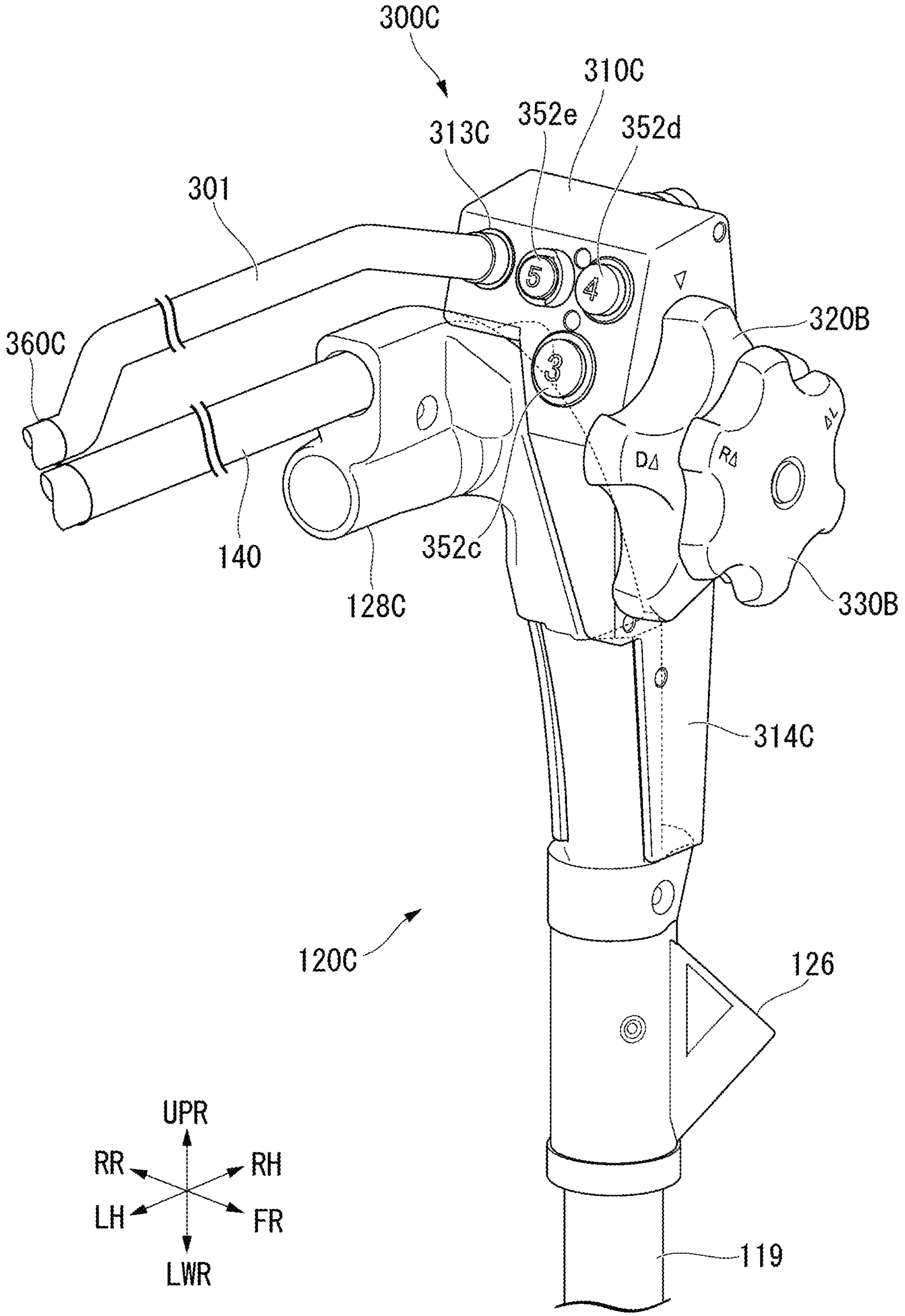
FIG. 28 is a perspective view of a modified example of the controller and connection portion of the medical manipulator system according to the second embodiment.
Figure 29:
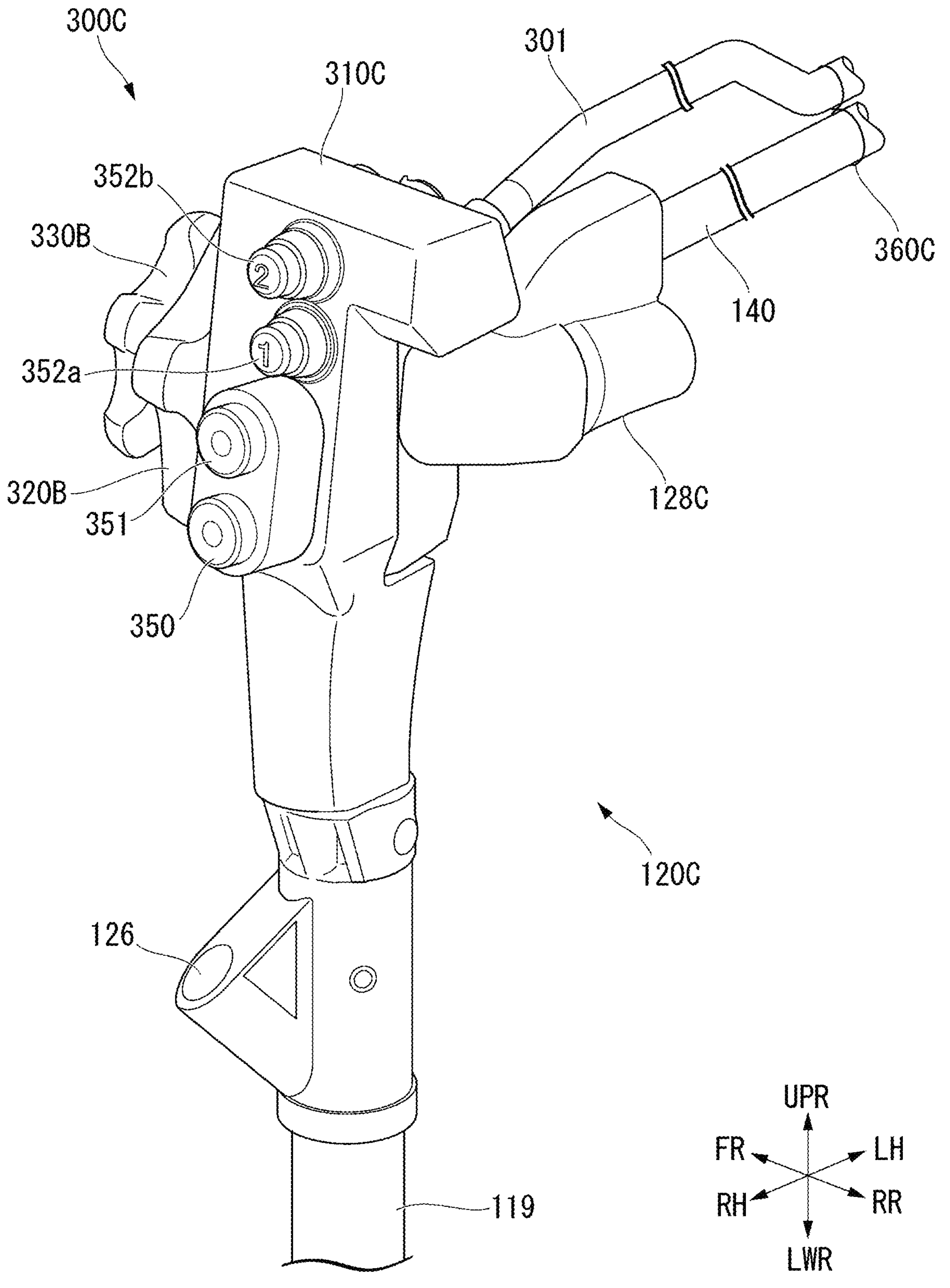
FIG. 29 is a perspective view of the modified example.
Figure 30:
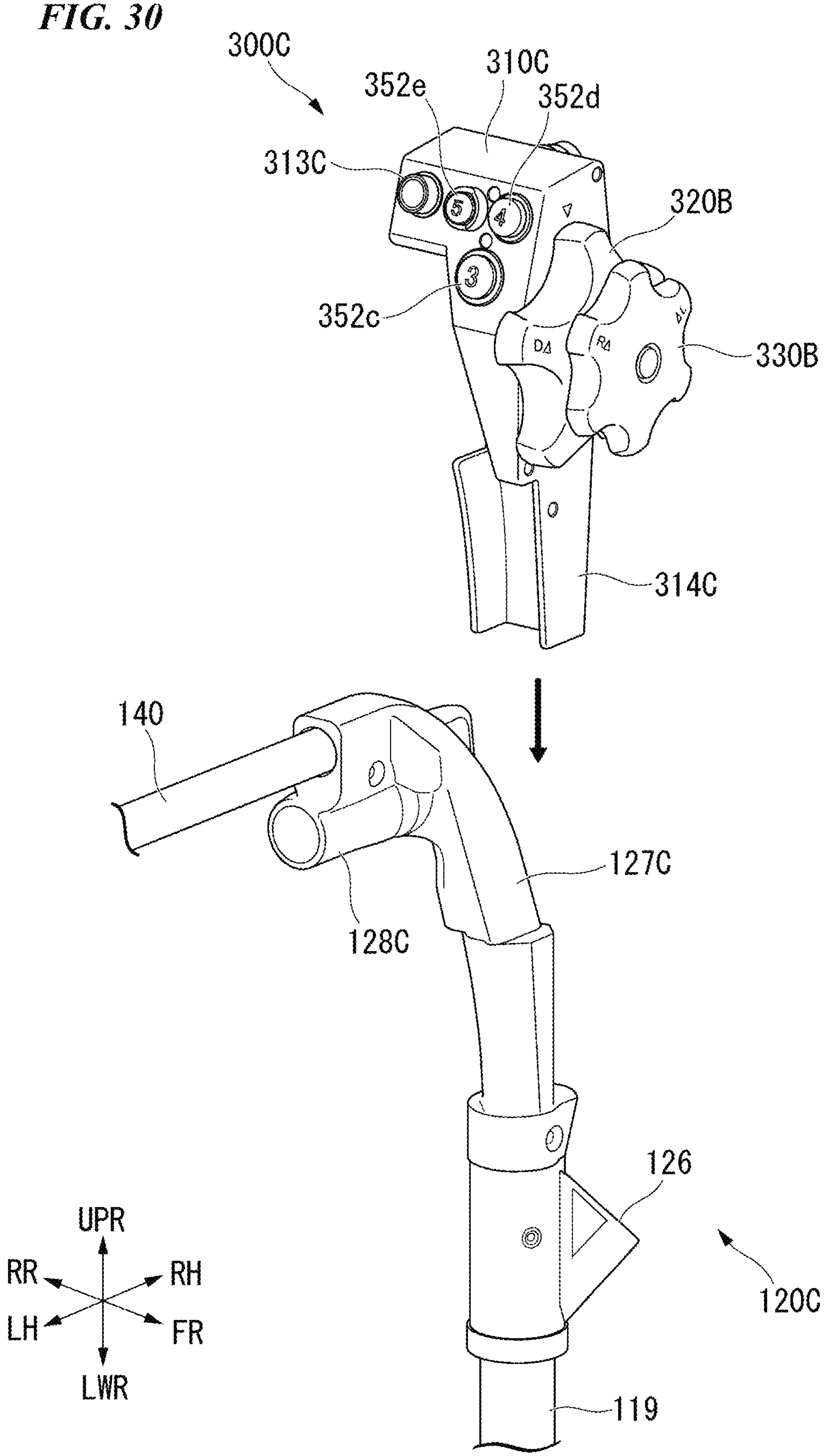
FIG. 30 is an exploded perspective view of the modified example.

FIG. 28 is a perspective view showing a controller 300C and a connection portion 120C. FIG. 29 is a perspective view showing a controller 300C and a connection portion 120C as seen from a direction different from FIG. 28. Also, FIG. 30 is an exploded perspective view of the controller 300C and the connection portion 120C.

As shown in FIGS. 28 and 29, the controller 300C and the connection portion 120C are connected and integrated. Also, as shown in FIG. 30, the controller 300C is removably connected to the connection portion 120C.

The controller 300C includes a manipulation portion body 310C, a first angle knob 320B, a second angle knob 330B, an air supply button 350, a suction button 351, a first button 352*a*, a second button 352*b*, a third button 352*c*, a fourth button 352*d*, and a fifth button 352*e*.

The manipulation portion body 310C includes a manipulation cable connection portion 313C to which the manipulation cable 301 is removably connected. Also, a cover portion 314C in which a substantially U-shaped cross-sectional shape extends in the upward/downward direction is formed on the manipulation portion body 310C in the downward direction LWR.

The controller 300C is removably connected to the drive device 200B via the manipulation cable 301 connected to the manipulation cable connection portion 313C. The controller 300C shown in FIG. 30 is the controller 300C in which the manipulation cable 301 is disconnected from the manipulation cable connection portion 313C.

The manipulation cable connection portion 313C is an adapter in which the manipulation cable 301 is removably connected to the manipulation portion body 310C. One end portion of the manipulation cable 301 is connected to the manipulation cable connection portion 313C and the other end portion is connected to the drive device 200B.

The cover portion 314C is provided on the manipulation portion body 310C in the downward direction LWR and is a substantially U-shaped portion having an opening in the left direction LH. The cover portion 314C extends from a portion located in the downward direction LWR slightly below the end portion of the first angle knob 320B in the downward direction LWR to the end portion of the controller 300C in the downward direction LWR.

The first button 352*a*, the second button 352*b*, the third button 352*c*, the fourth button 352*d*, and the fifth button 352*e* are buttons (switches) to which any function can be assigned. The first button 352*a* and the second button 352*b* are provided on the manipulation portion body 310C in the right direction RH. The third button 352*c*, the fourth button 352*d*, and the fifth button 352*e* are provided on the manipulation portion body 310C in the left direction LH. Also, the air supply button 350 and the suction button 351 are provided on the manipulation portion body 310C in the right direction RH.

The connection portion 120C is a member that connects the intracorporeal soft portion 119 and the extracorporeal soft portion 140. The connection portion 120C includes the forceps port 126 that is an insertion port for inserting the treatment tool 400. Also, as shown in FIG. 30, a connection portion body 127C has a substantially L-shaped shape. Therefore, the intracorporeal soft portion 119 and the extracorporeal soft portion 140 are connected at substantially right angles.

The intracorporeal soft portion 119 is connected to the end portion of the connection portion 120C in the downward direction LWR. Also, the extracorporeal soft portion 140 is connected to the connection portion 120C in the upward direction UPR so that it extends to the left direction LH.

Here, as shown in FIGS. 28 and 29, both the manipulation cable 301 connected to the manipulation portion body 310C and the extracorporeal soft portion 140 connected to the connection portion body 127C extend in the left direction LH. Therefore, as shown in FIGS. 28 and 29, when the physician S manipulates the controller 300C by bundling the manipulation cable 301 and the extracorporeal soft portion 140 using a bundling member 360C, the interference of the manipulation cable 301 or the extracorporeal soft portion 140 can be suppressed.

The bundling member 360C is, for example, a string-shaped member formed of rubber or the like.

In the vicinity of the portion bent at a substantially right angle of the connection portion body 127C, a gripped portion 128C is formed. As shown in FIG. 28, the gripped portion 128C is formed in the vicinity of a site to which the extracorporeal soft portion 140 is connected.

In the controller 300C connected to the connection portion 120C, the physician S puts the palm of his or her left hand L along the surface of the rearward direction RR and manipulates the first angle knob 320B or the second angle knob 330B with the thumb of his or her left hand L. At this time, the physician S manipulates the gripped portion 128C with the base of the thumb and the base of the index finger in support of the gripped portion 128C in the connection portion 120C bent at a substantially right angle. Therefore, the physician S can manipulate the controller 300C with manipulability (a hold feeling) close to that of the conventional flexible endoscope. Also, by providing the gripped portion 128C, a bending radius of the bending wire 160 inserted into the connection portion 120C can be increased.

By using the controller 300C and the connection portion 120C, the state can be easily switched between a state in which the controller 300C, the manipulation cable 301, and the connection portion 120C are connected (FIGS. 28 and 29) and a state in which each of the controller 300C, the manipulation cable 301, and the connection portion 120C is separated (FIG. 30).

The above-described components are implemented by recording a program in each embodiment on a computer-readable recording medium and causing a computer system to read and execute the program recorded on the recording medium. Also, the "computer system" used herein is assumed to include an operating system (OS) and hardware such as peripheral equipment. Also, the "computer-readable recording medium" refers to a flexible disk, a magneto-optical disc, a read-only memory (ROM), a portable medium such as a compact disc (CD)-ROM, or a storage device such as a hard disk embedded in the computer system. Furthermore, the "computer-readable recording medium" may include a computer-readable recording medium for dynamically holding the program for a short time period as in a communication line when the program is transmitted via a network such as the Internet or a communication circuit such as a telephone circuit and a computer-readable recording medium for holding the program for a given time period as in a volatile memory inside the computer system serving as a server or a client when the program is transmitted. Also, the above-described program may be a program for implementing some of the above-described functions. Furthermore, the above-described program may be a program capable of implementing the above-described function in combination with a program already recorded on the computer system.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

The above detailed description includes references to the accompanying drawings, which form a part of the detailed description. The drawings show, by way of illustration, specific embodiments that may be practiced. These embodiments are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is to allow the reader to quickly ascertain the nature of the technical disclosure and is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the embodiments should be determined with reference to the appended claims, along with the full scope of equivalents to which such claims are entitled.

What is claimed is:

1. A medical manipulator system comprising:
a medical manipulator comprising a bending portion configured to be bent;
an actuator configured to bend the bending portion;
an interface configured to receive an input of a bending manipulation for bending the bending portion, wherein the interface is configured to be moved by the bending manipulation from an origin; and
one or more processors configured to:
calculate an increase or a decrease in a ratio of a second angle to a rotation angle of the interface so that a difference between a first angle and the second angle is decreased, wherein:
the second angle is an angular displacement amount from a reference angle in the bending portion;
the reference angle is an angle of the bending portion when the interface is located at the origin; and
the first angle is calculated on the basis of a driving amount of the actuator; and
control the actuator to be driven on the basis of the calculated increase or decrease in the ratio.

2. The medical manipulator system according to claim 1, wherein the interface is configured to be moved in a first direction away from the origin and a second direction returning to the origin, and
wherein the one or more processors are configured to:
increase the ratio when the interface has moved in the first direction and decrease the ratio when the interface has moved in the second direction, when an absolute value of the first angle is less than an absolute value of the second angle; and
decrease the ratio when the interface has moved in the first direction and increase the ratio when the interface has moved in the second direction, when the absolute value of the first angle is greater than the absolute value of the second angle.

3. The medical manipulator system according to claim 2, further comprising:
a controller comprising:
the interface; and
an elastic member configured to bias the interface in the second direction, the interface being biased by the elastic member and moving into a passive control range when the interface is located on a side in the first direction rather than the passive control range that is a range closer to the origin, and
wherein, in controlling the actuator, the one or more processors are configured to:
control the actuator on the basis of a position of the interface when the interface is moving or when the interface is stopped outside of the passive control range; and
control the actuator on the basis of an external force applied to the medical manipulator when the interface is stopped within the passive control range.

4. The medical manipulator system according to claim 3, wherein the interface is rotatable in the first direction and the second direction, and
wherein the passive control range is a range of ±45° to ±90° from the origin.

5. The medical manipulator system according to claim 4, further comprising:
an imaging device provided at a distal end of the bending portion.

6. The medical manipulator system according to claim 5, wherein the interface comprises a lever, a knob, or a dial.

7. The medical manipulator system according to claim 6, wherein the elastic member is rubber or a spring.

8. The medical manipulator system according to claim 1, wherein the interface is configured to be moved at least in a first direction away from the origin and a second direction returning to the origin, and
wherein, in calculating the increase or the decrease in the ratio, the one or more processors are configured to:
perform a comparison of the first angle and the second angle;
perform a determination of one of the first direction and the second direction in which the interface is moved; and
calculate the increase or decrease in the ratio based on a result of the comparison and a result of the determination.

9. A control method for controlling a medical manipulator system, the medical manipulator system comprising:
a medical manipulator comprising a bending portion configured to be bent;
an actuator configured to bend the bending portion; and
an interface configured to receive an input of a bending manipulation for bending the bending portion, wherein the interface is configured to be moved by the bending manipulation from an origin,
wherein the control method comprises:
calculating an increase or a decrease in a ratio of a second angle to a rotation angle of the interface so that a difference between a first angle and the second angle is decreased, wherein:
the second angle is an angular displacement amount from a reference angle in the bending portion;
the reference angle is an angle of the bending portion when the interface is located at the origin; and
the first angle is calculated on the basis of a driving amount of the actuator; and
controlling the actuator to be driven on the basis of the calculated increase or decrease in the ratio.

10. The control method according to claim 9, wherein the interface is configured to be moved in a first direction away from the origin and a second direction returning to the origin, and
wherein calculating the increase or the decrease in the ratio comprises:
increasing the ratio when the interface has moved in the first direction and decreasing the ratio when the interface has moved in the second direction, when an absolute value of the first angle is less than an absolute value of the second angle; and
decreasing the ratio when the interface has moved in the first direction and increasing the ratio when the interface has moved in the second direction, when the absolute value of the first angle is greater than the absolute value of the second angle.

11. The control method for the medical manipulator system according to claim 10, wherein the medical manipulator system further comprises:

a controller comprising:

the interface; and an elastic member configured to bias the interface in the second direction, the interface being biased by the elastic member and moving into a passive control range when the interface is located on a side in the first direction rather than the passive control range that is a range closer to the origin, and wherein the controlling the actuator comprises:

controlling the actuator on the basis of a position of the interface when the interface is moving or when the interface is stopped outside of the passive control range; and controlling the actuator on the basis of an external force applied to the medical manipulator when the interface is stopped within the passive control range.

12. An apparatus for controlling a medical manipulator system comprising:

a medical manipulator comprising a bending portion configured to be bent;

an actuator configured to bend the bending portion; and an interface configured to receive an input of a bending manipulation for bending the bending portion, wherein the interface is configured to be moved by the bending manipulation from an origin, wherein the apparatus comprises one or more processors comprising hardware, wherein the one or more processors are configured to:

calculate an increase or a decrease in a ratio of a second angle to a rotation angle of the interface so that a difference between a first angle and the second angle is decreased, wherein:

the second angle is an angular displacement amount from a reference angle in the bending portion;

the reference angle is an angle of the bending portion when the interface is located at the origin; and the first angle is calculated on the basis of a driving amount of the actuator, and control the actuator to be driven on the basis of the calculated increase or decrease in the ratio.

13. The apparatus according to claim 12, wherein the interface is configured to be moved in a first direction away from the origin and a second direction returning to the origin, and wherein the one or more processors are configured to:

increase the ratio when the interface has moved in the first direction and decrease the ratio when the interface has moved in the second direction, when an absolute value of the first angle is less than an absolute value of the second angle; and decrease the ratio when the interface has moved in the first direction and increase the ratio when the interface has moved in the second direction, when the absolute value of the first angle is greater than the absolute value of the second angle.

14. The apparatus according to claim 13, wherein the medical manipulator system further comprises:

a controller comprising:

the interface; and an elastic member configured to bias the interface in the second direction, the interface being biased by the elastic member and moving into a passive control range when the interface is located on a side in the first direction rather than the passive control range that is a range closer to the origin, and wherein, in controlling the actuator, the one or more processors are configured to:

control the actuator on the basis of a position of the interface when the interface is moving or when the interface is stopped outside of the passive control range; and control the actuator on the basis of an external force applied to the medical manipulator when the interface is stopped within the passive control range.

* * * * *